United States Patent
Ghochikyan et al.

(10) Patent No.: US 10,570,196 B2
(45) Date of Patent: Feb. 25, 2020

(54) HUMANIZED ANTI-TAU ANTIBODIES AND COMPOSITIONS FOR AND METHODS OF MAKING AND USING IN TREATMENT, DIAGNOSIS AND MONITORING OF TAUOPATHIES

(71) Applicant: Anahit Ghochikyan, Huntington Beach, CA (US)

(72) Inventors: Anahit Ghochikyan, Huntington Beach, CA (US); Michael Agadjanyan, Huntington Beach, CA (US)

(*) Notice: Subject to any disclaimer, the term of this patent is extended or adjusted under 35 U.S.C. 154(b) by 0 days.

(21) Appl. No.: 16/316,345

(22) PCT Filed: Jul. 12, 2017

(86) PCT No.: PCT/US2017/041799
§ 371 (c)(1),
(2) Date: Jan. 8, 2019

(87) PCT Pub. No.: WO2018/017370
PCT Pub. Date: Jan. 25, 2018

(65) Prior Publication Data
US 2019/0292245 A1    Sep. 26, 2019

Related U.S. Application Data

(60) Provisional application No. 62/364,813, filed on Jul. 20, 2016.

(51) Int. Cl.
*C07K 16/18* (2006.01)
*A61K 39/00* (2006.01)

(52) U.S. Cl.
CPC ........ *C07K 16/18* (2013.01); *A61K 2039/505* (2013.01); *C07K 2317/24* (2013.01); *C07K 2317/34* (2013.01); *C07K 2317/567* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 2010/0324271 A1* | 12/2010 | Yamaguchi | C07K 16/44 530/387.3 |
| 2015/0196663 A1* | 7/2015 | Shusta | C07K 16/28 424/178.1 |
| 2015/0266947 A1* | 9/2015 | Sierks | G01N 33/6896 424/135.1 |
| 2017/0355756 A1* | 12/2017 | Julien | C07K 16/18 |

FOREIGN PATENT DOCUMENTS

WO    WO 2008068048    *    6/2008

OTHER PUBLICATIONS

Kussie "A Single Engineered Amino Acid Substitution Changes Antibody Fine Specificity" J immunol 152(1):146-52 (Year: 1994).*
Chen "Enhancement and destruction of antibody function by somatic mutation: unequal occurrence is controlled by V gene combinatorial associations" EMBO 14(12):2784-2794 (Year: 1995).*

* cited by examiner

*Primary Examiner* — Adam Weidner

(57) ABSTRACT

The disclosure provides methods of treating tauopathies (e.g. Alzheimer's disease, Amyotrophic Lateral Sclerosis, Frontotemporal Dementia with Parkinsonism linked to chromosome 17, Pick's Disease, Progressive Supranuclear Palsy, Dementia Pugilistica, Down's Syndrome and others) by administering humanized antibodies. The disclosure also provides the anti-tau humanized antibodies that bind the N-terminal region of tau and also bind to pathological tau aggregates, conformational epitopes and peptides mimicking these epitopes (mimotopes).

13 Claims, 25 Drawing Sheets
Specification includes a Sequence Listing.

(sequence illustration — SEQ ID NO.17 / SEQ ID NO.58)

(sequence illustration — SEQ ID NO.18 / SEQ ID NO.59)

```
      M  E  C  N  W  I  L  P  F  I  L  S  V  V  L  Q  G  L  T  Q  V  Q  L  Q  Q  S  G  P  V  L
  1  atggaatgta actggatact tcctttat ctgtaggtaa cttcagggt ctaccagag gttcagctcc agcaatctgg gactgtgctg A  R  P  G  A  S  V  K  M  S  C  K  T  S  G  Y  T  F  T  T  Y  W  I  N  W  V  K  Q  R  P
 91  gcagggctg gggttcagt gaagatgtcc tgtaaggctt ctggctacac atttacaacc tactggatac actggtaaa acagaggcct G  Q  G  L  E  W  I  G  N  I  Y  P  G  D  G  D  T  N  Y  N  Q  K  F  K  G  K  A  T  L
181  ggacaggtc tggaatggat aggg atatt tgtcctggag atagtgatac tagctacaac cagaagttca agggcaaggc caaactgact A  V  S  S  A  T  N  E  L  S  S  L  T  S  E  D  S  A  V  Y  Y  C  T  R  R  D  F
271  gcagtccat cctccagcac tgcctacatg gaactaagca gcctgacaat tgaggactct gcggtctatt actgtacaag aagggattc Y  G  S  D  Y  A  Y  D  Y  W  G  Q  G  T  S  V  T  V  S  S               SEQ ID NO.21
361  tacggtagtg actatgctgt ggactactgg ggtcaaggaa cctcagtcac cgtctcctca         SEQ ID NO.60
```

```
      M  K  L  P  V  R  L  L  V  L  M  F  W  I  P  A  S  S  S  D  V  V  M  T  Q  T  P  L  S  L
  1  atgaagttgc ctgttaggct gttggtgctg atgttctgga ttcctgcttc cagtagtgat gttgtgatga cccaaactcc actctcctg P  V  S  L  G  D  Q  A  S  I  S  C  R  S  S  Q  S  L  V  H  S  N  G  N  T  Y  L  H  W
 81  cctgtcagtc ttggagatca agcctccatc tcttgcagat ctagtcagag ccttgtacac agtaatggaa acacctatt acattggtac L  Q  K  P  G  Q  S  P  K  L  L  I  Y  K  V  S  N  R  F  S  G  V  P  D  R  F  S  G  S
181  ctgcagaagc caggccagtc tccaaaactc ctgatctaca aagtctccaa ccgattttct ggggtcccag acaggttcag tggcagtgga G  S  G  T  D  F  T  L  K  I  S  R  V  E  A  E  D  L  G  V  Y  F  C  S  Q  S  T  H  V  P
271  tcagggacag atttcacact caagatcaga agagtggagg ctgaggatct gggagtatat ttctgctctc aaagtacaca tgttccgtgg W  T  F  G  G  G  T  K  L  E  I  K                              SEQ ID NO.22
361  acgttcggtg gaggcaccaa gctggaaatc aaa                              SEQ ID NO.61
```

(Sequence illegible)

SEQ ID NO.19
SEQ ID NO.62

(Sequence illegible)

SEQ ID NO.20
SEQ ID NO.63

FIG. 9A
FIG. 9B
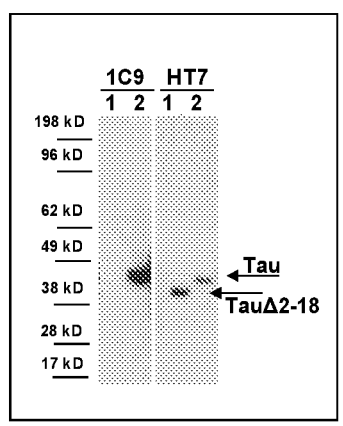
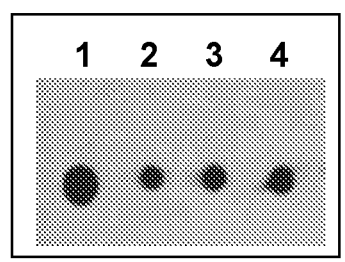
FIG. 9C
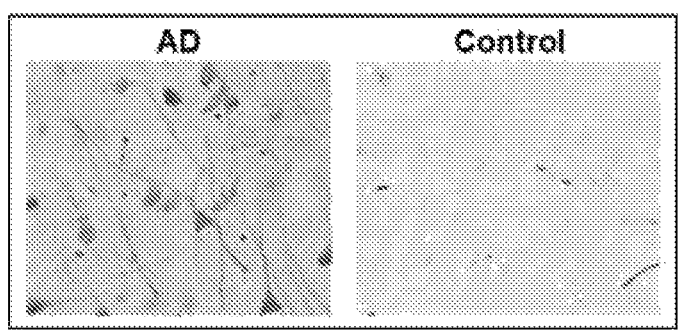
FIG. 9D
FIG. 9E
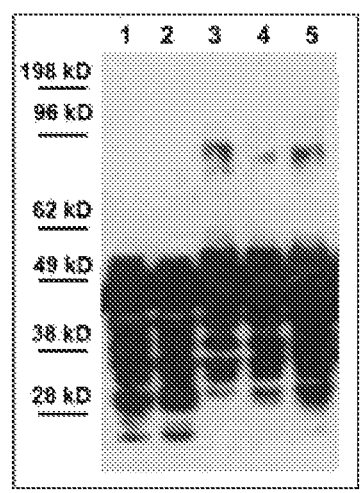
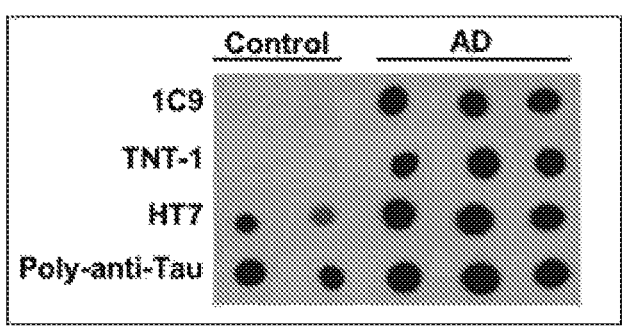

| mAb | kon (1/Ms) | koff (1/s) | KD (M) | Rmax (RU) | U-value |
|---|---|---|---|---|---|
| Mouse 1C9 | 1.27E+06 | 4.30E-03 | 3.39E-09 | 30.57 | 3 |
| Chimeric 1C9 | 1.53E+06 | 5.99E-03 | 3.91E-09 | 22.32 | 3 |

| mAb | $k_a$ (1/Ms) | $k_d$ (1/s) | $K_D$ (M) |
|---|---|---|---|
| Mouse 1C9 | 5.73E+05 | 5.45E-03 | 9.51E-09 |
| Humanized VH2+VL2 (Armanezumab) | 1.38E+05 | 6.64E-03 | 4.80E-08 |
| Humanized A17589 | 4.03E+05 | 8.37E-03 | 2.08E-08 |
| Humanized A17606 | 1.96E+05 | 3.60E-03 | 1.83E-08 |
| Humanized A17595 | 1.35E+05 | 3.40E-03 | 2.52E-08 |

FIG. 13A

Armanezumab VH

```
        M   G   W   S   W   I   L   L   F   L   L   S   V   T   A   G   V   H   S   Q
  1   atgggctgga gctggatcct gctgttcctc ctgagcgtga cagcaggagt gcacagccag V   Q   L   V   Q   S   G   A   E   V   K   K   P   G   A   S   V   K   V   S
 61   gtgcagctgg tgcagtctgg ggctgaggtg aagaagcctg gggcctcagt gaaggtttcc C   K   A   S   G   Y   T   F   T   N   H   W   M   H   W   V   R   Q   A   P
121   tgcaaggcat ctggatacac cttcaccaac cactggatgc actgggtgcg acaggcccct G   Q   G   L   E   W   M   G   A   I   D   P   G   N   S   D   T   S   Y   N
181   ggacaagggc ttgagtggat gggagctatt gatcctggaa atagtgatac tagctacaac Q   K   F   K   G   R   V   T   M   I   R   D   T   S   T   S   T   V   Y   M
241   cagaagttca agggcagagt caccatgacc agggacacgt ccacgagcac agtctacatg E   L   S   S   L   R   S   E   D   T   A   V   Y   Y   C   A   R   R   D   F
301   gagctgagca gcctgagatc tgaggacacg gccgtgtatt actgtgcgag gagggatttc F   G   E   Y   A   V   D   Y   W   G   Q   G   T   L   V   T   V   S   S           SEQ ID NO.80
361   ttcggtggtg agtatgctgt ggactactgg ggcagggaa ccctggtcac cgtctcctca          SEQ ID NO.70
```

FIG. 13B

Armanezumab VL

```
        M   G   W   S   W   I   L   L   F   L   L   S   V   T   A   G   V   H   S   D
  1   atgggctgga gctggatcct gctgttcctc ctgagcgtga cagcaggagt gcacagcgat I   V   M   T   Q   S   P   L   S   L   P   V   T   P   G   E   P   A   S   I
 61   attgtgatga ctcagtctcc actctccctg cccgtcaccc ctggagagcc ggcctccatc S   C   R   S   S   Q   S   L   V   H   S   N   G   N   T   Y   L   H   W   Y
121   tcctgcagat ctagtcagag ccttgtgcac agtaatggaa acacctattt acattggtac L   Q   K   P   G   Q   S   P   Q   L   L   I   Y   K   V   S   N   R   F   S
181   ctgcagaagc cagggcagtc tccacagctc ctgatctata aagtttccaa ccgattttct G   V   P   D   R   F   S   G   S   G   S   G   T   D   F   T   L   K   I   S
241   ggggtccctg acaggttcag tggcagtgga tcaggcacag attttacact gaaaatcagc R   V   E   A   E   D   V   G   V   Y   Y   C   S   Q   S   T   H   V   P   W
301   agagtggagg ctgaggatgt gggggtttat tactgctctc aaagtacaca tgttccgtgg T   F   G   Q   G   T   K   V   E   I   K                         SEQ ID NO.81
361   acgttcggcc aagggaccaa ggtggaaatc aaa                                SEQ ID NO.71
```

```
      M  G  W  S  W  I  L  L  F  L  L  S  V  T  A  G  V  H  S  E
  1 atgggctgga gctggatcct gctgttcctc ctgagcgtga cagcaggagt gcacagcgag V  Q  L  V  Q  S  G  A  E  V  K  K  P  G  A  T  V  K  I  S
 61 gtccagctgg tacagtctgg ggctgaggtg aagaagcctg gggctacagt gaaaatctcc C  K  V  S  G  Y  T  F  T  N  N  W  M  N  W  V  Q  Q  A  P
121 tgcaaggttt ctggatacac cttcaccaac aactggatga actgggtgca acaggccct G  K  G  L  E  W  M  G  A  I  D  P  G  N  S  D  T  S  Y  N
181 ggaaagggc ttgagtggat gggagctatt gatcctggaa atagtgatac tagctacaac Q  K  F  K  G  R  V  T  I  T  R  D  T  S  A  S  T  A  Y  M
241 cagaagttca agggcagagt caccattacc agggacacat ccgcgagcac agcctacatg E  L  S  S  L  R  S  E  D  T  A  V  Y  Y  C  A  R  R  D  F
301 gagctgagca gcctgagatc tgaagacacg gctgtgtatt actgtgcgag aagggattc F  G  G  K  Y  A  V  D  Y  W  G  Q  G  T  T  V  T  V  S            SEQ ID NO.82
361 ttcggtggtg agtatgctgt ggactactgg ggccagggga ccacggtcac cgtctcctc     SEQ ID NO.72
```

```
      M  G  W  S  W  I  L  L  F  L  L  S  V  T  A  G  V  H  S  D
  1 atgggctgga gctggatcct gctgttcctc ctgagcgtga cagcaggagt gcacagcgat I  V  M  T  Q  T  P  L  S  L  S  V  T  P  G  Q  P  A  S  I
 61 attgtgatga cccagactcc actctctctg tccgtcaccc ctggacagcc ggcctccatc S  C  R  S  S  Q  S  L  V  N  S  N  G  N  T  Y  L  N  W  Y
121 tcctgcagat ctagtcagag ccttgtgaac agtaatggaa acacctattt acattggtac Q  Q  K  P  G  Q  A  P  R  L  L  I  Y  K  V  S  N  R  F  S
181 cagcagaaac ctggccaggc tcccaggctc ctcatctata aagtttccaa ccgattttct G  V  P  D  R  F  S  G  S  G  A  G  T  D  F  T  L  K  I  S
241 ggggtcccag acagattcag tggcagtggg gcaggacag atttcacact gaaaatcagc R  V  E  A  E  D  V  G  V  Y  Y  C  S  Q  S  T  N  V  P  N
301 agggtggaag ctgaggatgt cggggtttat tactgctctc aaagtacaca tgttccgtgg T  F  G  G  G  T  K  V  E  I  K                    SEQ ID NO.83
361 acgttcggcg gagggaccaa ggtggagatc aaa                 SEQ ID NO.73
```

```
      M   G   W   S   W   I   L   L   F   L   L   S   V   T   A   G   V   H   S   Q
  1 atgggctgga gctggatcct gctgttcctc ctgagcgtga cagcaggagt gcacagccag V   Q   L   V   Q   S   G   A   E   V   K   K   P   G   A   S   V   K   V   S
 61 gtccagcttg tgcagtctgg ggctgaggtg aagaagcctg gggcctcagt gaaggtttcc C   K   A   S   G   Y   T   F   T   N   N   W   M   H   W   V   Q   Q   S   P
121 tgcaaggctt ctggatacac cttcactaac cactggatgc actgggtgca acagtccct G   Q   G   L   E   W   M   G   A   I   D   P   G   N   S   D   T   S   Y   N
181 ggacaagggc ttgagtggat gggagctatt gatcctggaa atagtgatac tagctacaac Q   K   F   K   G   R   V   T   M   T   R   D   T   S   T   S   T   V   Y   M
241 cagaagttca agggcagagt caccatgacc agggacacgt ccacgagcac agtctacatg E   L   S   S   L   R   S   E   D   T   A   V   Y   Y   C   A   R   R   D   F
301 gagctgagca gcctgagatc tgaggacacg gccgtgtatt actgtgcgag aagggattc F   G   K   Y   A   V   D   Y   W   G   Q   G   T   T   V   T   V   S   S         SEQ ID NO.84
361 ttcggtggtg agtatgctgt ggactactgg ggccaaggga ccacggtcac cgtctcctca        SEQ ID NO.74
```

```
      M   G   W   S   W   I   L   L   F   L   L   S   V   T   A   G   V   H   S   D
  1 atgggctgga gctggatcct gctgttcctc ctgagcgtga cagcaggagt gcacagcgac I   Q   M   T   Q   S   P   S   S   L   S   A   S   V   G   D   R   V   T   I
 61 atccagatga cccagtctcc atcctccctg tctgcatctg taggagacag agtcaccatc T   C   R   S   S   Q   S   L   V   H   S   N   G   N   T   Y   L   H   W   Y
121 acttgcagat ctagtcagag ccttgtgcac agtaatggaa acacctattt acattggtat Q   Q   K   P   G   K   A   P   K   L   L   I   Y   K   V   S   N   R   F   S
181 cagcagaaac cagggaaagc ccctaagctc ctgatctata aagtttccaa ccgattttct G   V   P   D   R   F   S   G   S   G   S   G   T   D   F   T   L   K   I   S
241 gggtcccag acagattcag cggcagtggg tcaggcactg atttcacact gaaaatcagc R   V   E   A   E   D   V   G   V   Y   Y   C   S   Q   S   T   H   V   P   W
301 agggtggagg ctgaggatgt tggggtttat tactgctctc aaagtacaca tgttccgtgg T   F   G   G   G   T   K   V   E   I   K         SEQ ID NO.85
361 acgttcggcg agggaccaa ggtggagatc aaa        SEQ ID NO.75
```

```
      M  G  W  S  W  I  L  L  F  L  L  S  V  T  A  G  V  H  S  Q
  1 atgggctgga gctggatcct gctgttcctc ctgagcgtga cagcaggagt gcacagccag V  Q  L  V  Q  S  G  S  E  L  K  K  P  G  A  S  V  K  V  S
 61 gtgcagctgg tgcaatctgg gtctgagttg aagaagcctg ggcctcagt gaaggtttcc C  K  A  S  G  Y  T  F  T  N  H  W  M  H  W  V  R  Q  A  P
121 tgcaaggctt ctggatacac cttcactaac cactggatgc actgggtgcg acaggcccct G  Q  G  L  E  W  M  G  A  I  D  P  E  N  S  D  T  S  Y  N
181 ggacaagggc ttgagtggat gggagctatt gatcctggaa atagtgatac tagctacaac Q  K  F  K  G  Q  V  T  I  S  A  D  K  S  I  S  T  A  Y  L
241 cagaagttca agggccaggt caccatctca gccgacaagt ccatcagcac cgcctacctg Q  W  S  S  L  K  A  S  D  T  A  M  Y  Y  C  A  R  R  D  F
301 cagtggagca gcctgaaggc ctcggacacc gccatgtatt actgtgcgag aagggatttc F  G  E  Y  A  V  D  Y  W  G  Q  G  T  T  V  T  V  S  S       SEQ ID NO.86
361 ttcggtggtg agtatgctgt ggactactgg ggccaaggga ccacggtcac cgtctcctca  SEQ ID NO.76
```

```
      M  G  W  S  W  I  L  L  F  L  L  S  V  T  A  G  V  H  S  D
  1 atgggctgga gctggatcct gctgttcctc ctgagcgtga cagcaggagt gcacagcgat I  V  M  T  Q  T  P  L  S  L  S  V  T  P  G  Q  P  A  S  I
 61 attgtgatga cccagactcc actctctctg tccgtcaccc ctggacagcc ggcctccatc S  C  R  S  S  Q  S  L  V  H  S  N  G  N  T  Y  L  H  W  Y
121 tcctgcagat ctagtcagag ccttgtgcac agtaatggaa acacctattt acattggtac Q  Q  K  P  G  Q  A  P  R  L  L  I  Y  K  V  S  N  R  F  S
181 cagcagaaac ctggccaggc tcccaggctc ctcatctata aagtttccaa ccgattttct G  V  P  D  R  F  S  G  S  G  S  G  T  D  F  T  L  K  I  S
241 ggagtgccag ataggttcag tggcagcggg tcaggacag atttcacact gaaaatcagc R  V  E  A  E  D  F  G  V  Y  Y  C  S  Q  S  T  H  V  P  W
301 cgggtggagg ctgaggattt tggagtttat tactgctctc aaagtacaca tgttccgtgg T  F  G  G  G  T  K  V  E  I  K                SEQ ID NO.87
361 acgttcggcg gagggaccaa ggtggagatc aaa             SEQ ID NO.77
```

```
      M  G  W  S  W  I  L   L  F  L   L  S  V  T   A  G  V   H  S  E
  1 atgggctgga gctggatcct gctgttcctc ctgagcgtga cagcaggagt gcacagcgag V  Q  L  V  E  S  G   G  G  L   V  Q  P  G   G  S  L   R  L  S
 61 gtgcagctgg tggagtccgg gggaggcttg gtccagcctg ggggtccct gaaactctcc C  A  A  S  G  F  T   F  S  N   H  W  M  S   W  V  R   Q  A  S
121 tgtgcagcct ctgggttcac cttcagtaac cactggatgc actgggtccg ccaggcttcc G  K  G  L  E  W  V   A  I  D   P  G  N  S   D  T  S   Y  N
181 gggaaagggc tggagtgggt tgcgctatt gatcctggaa atagtgatac tagctacaac Q  K  F  K  G  R  F   T  I  S   R  D  D  S   K  N  T   A  Y  L
241 cagaagttca agggcaggtt caccatctcc agagatgatt caaagaacac ggcgtatctg Q  M  N  S  L  K  T   E  D  T   A  V  Y  Y   C  T  R   R  D  F
301 caaatgaaca gcctgaaaac cgaggacacg gccgtgtatt actgtactag aagggatttc F  G  G  E  Y  A  V   D  Y  W   G  Q  G  T   T  V  T   V  S  S          SEQ ID NO.88
361 ttcggtggtg agtatgctgt ggactactgg ggccaaggga ccacggtcac cgtctcctca          SEQ ID NO.78
```

```
      M  G  W  S  W  I  L   L  F  L   L  S  V  T   A  G  V   H  S  D
  1 atgggctgga gctggatcct gctgttcctc ctgagcgtga cagcaggagt gcacagcgat I  V  M  T  Q  T  P   L  S  L   S  V  T  P   G  Q  P   A  S  I
 61 attgtgatga cccagactcc actctctctg tccgtcaccc ctggacagcc ggcctccatc S  C  R  S  S  Q  S   L  V  H   S  N  G  N   T  Y  L   N  W  Y
121 tcctgcagat ctagtcagag ccttgtgcac agtaatggaa acacctattt acattggtac Q  Q  K  P  G  Q  A   P  R  L   L  I  Y  K   V  S  N   R  F  S
181 cagcagaaac ctggccaggc tccaggctc ctcatctata aagttccaa ccgatttct G  V  P  D  R  F  S   G  S  G   A  G  T  D   F  T  L   K  I  S
241 gggtcccag acagattcag tggcagtggg gcagggacag atttcacact gaaaatcagc R  V  E  A  E  D  V   G  V  Y   Y  C  S  Q   S  T  H   V  P  W
301 agggtggaag ctgaggatgt cggggtttat tactgctctc aaagtacaca tgttccgtgg T  F  G  G  G  T  K   V  E  I   K          SEQ ID NO.89
361 acgttcggcg gagggaccaa ggtggagatc aaa          SEQ ID NO.79
```

HUMANIZED ANTI-TAU ANTIBODIES AND COMPOSITIONS FOR AND METHODS OF MAKING AND USING IN TREATMENT, DIAGNOSIS AND MONITORING OF TAUOPATHIES

STATEMENT REGARDING SEQUENCE LISTING

The sequence listing associated with this application is provided in text format in lieu of a paper copy, and is hereby incorporated by reference into the specification. The name of the text file containing the sequence listing is AGPT-seq-list.txt; the text file is 58,800 bytes, was created on Jul. 12, 2017, and is being submitted electronically via EFS-web.

TECHNICAL FIELD

This patent application relates generally to antibodies that react with tau and methods using these antibodies in treatment of tauopathies, including Alzheimer's Disease.

BACKGROUND

Misfolding and aggregation of some specific proteins is a hallmark of a variety of neurodegenerative disorders, including but not limited to Alzheimer's Disease (AD) and frontotemporal dementia. Attention and research has focused primarily on deposition of amyloid-$\beta$ (A$\beta$) in senile plaques, although aggregation of pathological tau protein in neurofibrillary tangles also plays an important role in disease progression (Ballatore C. et al., Nat Rev Neurosci 2007, 8, 663-672).

Tau is a microtubule-associated protein. In AD, tau undergoes several changes to a pathological state. Tau can be abnormally folded and phosphorylated resulting in the generation of neurofibrillary tangles toxic to neurons. In AD, amyloid accumulation in the brain can occur decades before the beginning of symptoms such as memory loss and personality change. Current data suggest that A$\beta$ pathology emerges prior to tau pathology, but may accelerate toxic neurofibrillary tangle formation. At best however, anti-A$\beta$ immunotherapy only slightly decreases tau pathology and often does not affect the level of pathological tau at all. Moreover, pathological tau burden in the brains of patients with mild to moderate AD plays an important role in disease progression.

SUMMARY

The disclosure is directed to humanized antibodies that recognize and bind to an epitope in the N-terminal region of pathological neurotoxic forms of tau.

These and other aspects of the present invention will become evident upon reference to the following detailed description and attached drawings.

BRIEF DESCRIPTION OF THE DRAWINGS

FIG. 1 shows humoral (FIG. 1A and FIG. 1B) and cellular (FIG. 1C) responses in B6SJL immunized with $tau_{2-18}$ fused with MultiTEP carrier protein. Mice were immunized biweekly (3 times) with 40 µg/mouse $tau_{2-18}$-MultiTEP vaccine or irrelevant control peptide formulated in Quil-A adjuvant.

FIG. 3 demonstrates inhibition of trans-cellular propagation of tau aggregates by anti-$tau_{2-18}$ antibody. HEK293 cells transfected with RD(LM)-HA or mock transfected (NT) were co-cultured for 48 h with an equivalent number of HEK293f cells co-transfected with RD($\Delta$K)-CFP ($\Delta$K-C) and RD($\Delta$K)-YFP ($\Delta$K-Y) prior to FRET analysis. Increased FRET signal was detected in cells co-cultured with cells transfected with RD(LM)-HA. Addition of serial dilutions of purified anti-$tau_{2-18}$ antibody decreased FRET signal due to inhibition of trans-cellular propagation of aggregated RD.

FIG. 6A and FIG. 6B depict amino acid sequence VH and VL chains of mouse monoclonal antibody 1C9 and a nucleotide sequence encoding the amino acid sequence. CDRs are bold and underlined.

FIG. 7A and FIG. 7B depict amino acid sequence VH and VL chains of mouse monoclonal antibody 2F6/H11 and a nucleotide sequence encoding the amino acid sequence. CDRs are bold and underlined.

FIG. 8A and FIG. 8B depicts amino acid sequence VH and VL chains of mouse monoclonal antibody 4F3/H1 and a nucleotide sequence encoding the amino acid sequence. CDRs are bold and underlined.

FIG. 9 shows the characterization of mouse 1C9 anti-$tau_{2-18}$ monoclonal antibody. FIG. 9A shows that 1C9 recognized full-length tau but not tau that lacks 2-18 domain in Western Blot. Lane 1—tau$\Delta$2-18, lane 2—full-length tau. FIG. 9B shows that 1C9 bound monomeric (spot 1), oligomeric (spot 2: cross-linked; spot 3: non-cross-linked) and fibrillar (spot 4) forms of recombinant tau protein in dot blot. FIG. 9C shows anti-$tau_{2-18}$ mAb 1C9 bound to neuropil threads and neurofibrillary tangles in AD brains (Braak stage VI-C). No binding was observed with non-AD brain (Braak stage 0). Original magnification 40×, scale bar=20 um. FIG. 9D shows that 1C9 bound different species of tau protein in brain homogenates from both AD cases and control subjects in denaturing conditions (lane 1: control 1; lane 2—control 2; lane 3—AD1; lane 4—AD2; lane 5—AD3) in Western Blot. FIG. 9E shows that in non-denaturing conditions in Dot Blots 1C9 as well as commercial TNT-1 Ab specific to N-terminus of Tau selectively bound to soluble tau in AD brains but not in controls, while HT7 and rabbit anti-tau-polyclonal Ab recognizing total tau, had bound tau in both control and AD brains.

FIG. 13A and FIG. 13B depict amino acid sequence of humanized VH and VL chains of Armanezumab and a nucleotide sequence encoding the amino acid sequence. CDRs are bold and underlined.

FIG. 14A and FIG. 14B depict amino acid sequence of humanized VH and VL chains of A17589 and a nucleotide sequence encoding the amino acid sequence. CDRs are bold and underlined.

FIG. 15A and FIG. 15B depicts amino acid sequence of humanized VH and VL chains of A17595 and a nucleotide sequence encoding the amino acid sequence. CDRs are bold and underlined.

FIG. 16A and FIG. 16B depicts amino acid sequence of humanized VH and VL chains of A17606 and a nucleotide sequence encoding the amino acid sequence. CDRs are bold and underlined.

FIG. 17A and FIG. 17B depicts amino acid sequence of humanized VH and VL chains of VH3+VH2 and a nucleotide sequence encoding the amino acid sequence. CDRs are bold and underlined.

FIG. 18 shows binding specificity of Armanezumab.

FIG. 23 shows that passive vaccination with 1C9 moAb, mouse counterpart of Armanezumab, administered intraperitoneally, improved recognition memory of vaccinated mice compared with mice injected with control mouse IgG.

DETAILED DESCRIPTION

Figure 1A:
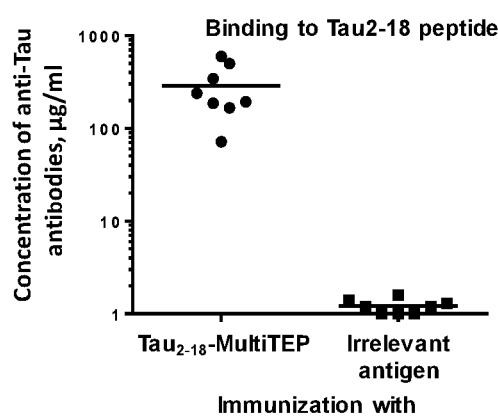
FIG. 1A shows titers of antibodies specific to $tau_{2-18}$ peptide determined in serially diluted individual sera. Lines indicate the average of titers in experimental (n=8) and control (n=8) groups of mice.

The present disclosure provides humanized antibodies, including antibody fragments, single-chain antibodies, chimeric antibodies and other forms of antibodies specific to pathological tau aggregates, immunogenic tau peptides and tau antigens or mimotope. The disclosure also provides constructs and cells producing these humanized antibodies. The disclosure also provides uses of these antibodies and their pharmaceutical compositions in the treatment of tauopathies and provides uses of the antibodies for diagnosis and monitoring of tauopathies. The disclosure also provides a method of treating tauopathy in an individual, the method comprising administering to the individual an anti-tau antibody of the present disclosure, or a pharmaceutical composition of the present disclosure.

1. Tau Protein and Peptides

Tau protein or fragment of tau is used as an antigen to generate an immune response. Tau is a microtubule-associated protein found primarily in neurons and glia, but also in other areas of the CNS. Six isoforms have been identified, primarily differing by their number of binding domains. The isoforms result from alternative splicing. Three isoforms have three binding domains (3R), and three have four (4R). Exons 2 and 3 are variably present. In two isoforms, both are present (2N), in two other isoforms, just exon 3 is present (1N), and in two, neither are present (0N). The binding domains of tau are located in the C-terminus region. The six isoforms are called 0N3R (SEQ ID NO.1), 0N4R (SEQ ID NO.2), 1N3R (SEQ ID NO.3), 1N4R (SEQ ID NO.4), 2N3R (SEQ ID NO.5), and 2N4R (SEQ ID NO. 6). In addition, tau may be phosphorylated. Aggregation of tau proteins is a common feature of numerous neurodegenerative disorders.

The N-terminal region of tau is normally folded to the interior of the protein, but it is exposed during aggregation of tau (Morfini, G. A. et al. J Neurosci, 2009, 29, 12776-12786; Horowitz, P. M. et al,. J Neurosci 2004, 24, 7895-7902). It is also termed as phosphatase-activating domain (PAD) and plays a role in activation of a signalling cascade involving protein phosphatase I and glycogen synthase kinase 3, which leads to anterograde FAT inhibition. The N-terminal region may be used to generate antibodies to tau. The N-terminal region may be from residues about 1 to about 100, from about 1 to about 50, from about 1 to about 25, from about 1 to about 20, from 1 to about 15. In certain embodiments, the region starts at residue 2 and extends to about residue 100, about residue 50, about residue 25, about residue 20, or about residue 15. In certain embodiments, the region is from residue 2 through 18 and comprises the sequence AEPRQEFEVMEDHAGTY (SEQ ID NO.7), called $tau_{2-18}$.

In another embodiments, the region is from residue 2 through 36 and comprises the sequence AEPRQEFEVMED-HAGTYGLGDRKDQGGYTMHQDQE (SEQ ID NO. 8), called $tau_{2-36}$. The region used for the generation of anti-tau antibodies is referred to herein as "tau antigen". It is preferable that the tau antigen be non-phosphorylated. Other regions may also be used to generate anti-tau therapeutic antibodies.

A tau antigen should be able to induce a humoral immune response. Verification that a candidate antigen induces a humoral response can be performed by a variety of methods. In one method, the protein sequence of the antigen is synthesized and coupled to a carrier protein that is used to immunize an animal, e.g. a mouse. Sera may then be tested by ELISA or other known method for the presence of antibodies to the candidate. In addition, the epitopes may be tested by any method known in the art or described herein for stimulation of T cells. Suitable epitopes do not stimulate T cells detectably.

Depending on size and immunogenicity, among other factors, the tau antigen may be coupled to a carrier molecule, typically a protein. Carrier proteins are well-known in the art and include tetanus toxin, diphtheria toxoid, Hepatitis B surface antigen, influenza virus hemagglutinin, influenza virus matrix protein, serum albumin, and the like. In some embodiments, fragments of the carrier proteins are used.

2. Antibodies to Tau

Antibodies to tau are provided herein. Antibodies are raised to the N-terminal region of tau, and in certain embodiments, to $tau_{2-18}$. In another embodiments antibodies are raised to the $tau_{2-36}$. Antibodies should bind an epitope in the N-terminal region of tau. In some embodiments, the antibodies are capable of binding to the repeat domain (RD) of tau, to aggregated RD domains, to recombinant human tau; to pathologically modified tau; to pathologically aggregated tau at the pre-tangle stage, in neurofibrillary tangles (NFT), neuropil threads and dystrophic neurites in the brain; to any of the six tau isoforms; to amino acids 2-18 of tau; to amino acids 2-36, to a conformational antigenic determinant that occurs in the pathological form of tau; or to a peptide mimicking (mimotope) the tau conformational antigenic determinant.

Antibodies that bind pathological tau, but not normal tau, are highly desirable, although in general, anti-tau antibodies are not internalized in cells where they could bind functionally normal tau molecules. Antibodies may be used for a variety of purposes, including isolation of tau and inhibiting (antagonist) activity of tau, especially pathological forms of tau. As well, assays for small molecules that interact with pathological tau will be facilitated by the development of antibodies.

Within the context of the present invention, antibodies are understood to include monoclonal antibodies, polyclonal antibodies, anti-idiotypic antibodies, single chain antibodies, chimeric antibodies, antibody fragments (e.g., Fab', Fab, and F(ab')2, Fv variable regions, single chain Fv, or complementarity determining regions). Antibodies are generally accepted as specific against tau protein if they bind with a Kd equal to or greater than $10^{-7}$M, preferably equal to or greater than $10^{-8}$M. The affinity of an antibody or binding partner can be readily determined by one of ordinary skill in the art (see Scatchard, G. Annals of the New York Academy of Sciences, 1949, 51, 660-672).

Monoclonal antibodies may also be readily generated from hybridoma cell lines using conventional techniques (see U.S. Pat. No. RE 32,011, U.S. Pat. Nos. 4,902,614, 4,543,439, and 4,411,993; see also Antibodies: A Laboratory Manual, Harlow and Lane (eds.), Cold Spring Harbor Laboratory Press, 1988; all references incorporated in their entirety). Briefly, within one embodiment, a subject animal such as a rat or mouse is injected with one of the compositions taught herein. Protein are typically administered as an emulsion in an adjuvant such as Freund's complete or incomplete adjuvant, QuilA and others in order to increase the immune response. Nucleic acid constructs are administered using devices such as gene gun or electroporation device. Between one and three weeks after the initial immunization, the animal is generally boosted and may tested for reactivity to tau utilizing well-known assays. The spleen and/or lymph nodes are harvested and cells immortalized. Various immortalization techniques, such as mediated by Epstein-Barr virus or fusion to produce a hybridoma, may be used. In one embodiment, immortalization occurs by fusion with a suitable myeloma cell line to create a hybridoma that secretes monoclonal antibody. Suitable myeloma lines include, for example, NS-1 (ATCC No. TIB 18), and P3X63—Ag 8.653 (ATCC No. CRL 1580). Preferred fusion partners do not express endogenous antibody genes. Following fusion, the cells are cultured in medium containing a reagent that selectively allows for the growth of fused cells. After about seven days, hybridomas may be screened for the presence of antibodies that are reactive against a tau protein. A wide variety of assays may be utilized, including for example counter current immuno-electrophoresis, radioimmunoassays, radioimmunoprecipitations, enzyme-linked immuno-sorbent assays (ELISA), dot blot assays, western blots, immunoprecipitation, inhibition or competition assays, and sandwich assays (see U.S. Pat. Nos. 4,376, 110 and 4,486,530, incorporated in their entirety; see also Antibodies: A Laboratory Manual, Harlow and Lane (eds.), Cold Spring Harbor Laboratory Press, 1988).

Other techniques may also be utilized to construct monoclonal antibodies (see Huse, W. D. et al., Science, 1989, 246, 1275-1281; Sastry, L. et al., Proc Natl Acad Sci USA, 1989, 86, 5728-5732; Alting-Mees, M. e. a. Strategies in Molecular Biology, 1990, 3, 1-9). Briefly, mRNA is isolated from a B cell population and utilized to create heavy and light chain immunoglobulin cDNA expression libraries in suitable vectors, such as *ImmunoZap(H) and *ImmunoZap(L). These vectors may be screened individually or co-expressed to form Fab fragments or antibodies (see Huse, W. D. et al., Science, 1989, 246, 1275-1281; Sastry, L. et al., Proc Natl Acad Sci USA, 1989, 86, 5728-5732). Positive plaques may subsequently be converted to a non-lytic plasmid that allows high level expression of monoclonal antibody fragments from *E. coli*.

Similarly, portions or fragments, such as Fab and Fv fragments, of antibodies that contain the antigen-binding site may also be constructed utilizing conventional enzymatic digestion or recombinant DNA techniques to yield isolated variable regions of an antibody. In one embodiment, the genes which encode the variable region from a hybridoma producing a monoclonal antibody of interest are amplified using nucleotide primers for the variable region. These primers may be synthesized by one of ordinary skill in the art, or may be purchased from commercially available sources (e.g., Stratacyte, La Jolla, Calif.) Amplification products are inserted into vectors such as ImmunoZAP™ H or ImmunoZAP™ L (Stratacyte), which are then introduced into *E. coli*, yeast, insect cells, or mammalian-based systems for expression. Utilizing these techniques, large amounts of a single-chain protein containing a fusion of the VH and VL domains (scFv) may be produced (Bird, R. E. et al., Science, 1988, 242, 423-426). In addition, techniques may be utilized to change a "murine" antibody to a "human" antibody, without altering the binding specificity of the antibody (U.S. Pat. Nos. 5,225,539, 5,530,101, 6,331,415, all incorporated in their entirety).

Once suitable antibodies have been obtained, they may be isolated or purified by many techniques well known to those of ordinary skill in the art (see Antibodies: A Laboratory Manual, Harlow and Lane (eds.), Cold Spring Harbor Laboratory Press, 1988). Suitable techniques include peptide or protein affinity columns, HPLC or RP-HPLC, purification on protein A or protein G columns, or any combination of these techniques.

3. Humanization of Antibodies

A humanized antibody is an antibody originating from a non-human species whose protein sequence has been modified to increase its similarity to antibodies produced naturally in humans. The process of humanization is usually applied to monoclonal antibodies. The amount of non-human sequence can range from just the CDR sequences to the entire V region. Although typically, both the light and heavy chain will have some human sequence, a humanized antibody may have human sequence in only one of the two chains (e.g., a human Fc region). For purposes herein, "humanized antibody" refers to an antibody that contains some amount of human sequence. In certain embodiments, the humanized antibody has human constant regions and the variable regions are non-human. In certain other embodiments, only the CDR sequences are non-human. Techniques to humanize an antibody are well known and widely practiced.

In a fully humanized antibody (only the CDR sequences are non-human), the framework (FR) segments of the variable region may be from any of the families and moreover, may be from different families. The constant regions of the light chain may be either kappa or lambda, the constant regions of the heavy chain may be of the $\mu$, $\gamma$, $\alpha$, $\epsilon$, or $\delta$ type, although typically will be one of the four $\gamma$ subclasses. Generally, all the domains of the constant region will be from the same class (e.g., all from class $\gamma 1$).

Framework segments may be chosen on a variety of bases. For example, human framework sequences that share the highest identities to the framework sequences of the non-human antibody can be chosen. Another basis is selection of the humanized antibodies with the highest binding affinity or avidity. Binding affinity of antibodies to tau protein can be determined by a variety of methods, including surface plasmon resonance (SPR) analysis.

In an exemplary method, a mouse monoclonal antibody was initially humanized by replacement of the constant regions of heavy and light chains with human sequences. Binding affinity of the chimeric antibody to tau was verified as equivalent to the parental (murine) antibody. The chimeric antibody was further humanized by replacing the heavy and light chain variable region frameworks with human frameworks. The human FR1, FR2, FR3, which shared the highest identities with those of the mouse antibody were selected and assembled with mouse CDRs using overlapping PCR. Amplified fragments were inserted into a phage display vector to create a library of phage expressing humanized Fab fragments. Strong binders to recombinant tau protein were selected through three rounds of panning. Highest affinity antibodies were chosen.

The humanized antibodies can be readily produced in cells. DNA sequence analysis of antibodies can be used to construct expression vectors. The sequences of the CDRs is the minimum information needed to construct a humanized antibody. In certain embodiments the DNA sequence encoding a fully humanized antibody or Fab fragment is obtained. As disclosed below, the DNA sequence is inserted in an expression vector. The expression vector is transduced into cells and antibody protein is produced. The cells may be prokaryotic or eukaryotic. Vectors and host cells are well known and readily obtainable for production of protein.

Antibodies may be recovered from cells or cell supernatant. They may be used with or without concentration, and with or without further purification. If purified, a typical method is HPLC, although alternative purification methods such as ion exchange chromatography and gel filtration chromatography may be used. Acceptable purity is at least 90% or at least 95% or at least 98% as assessed by analytical HPLC.

4. Construction of DNA Compositions

When antibodies are to be delivered as a DNA composition or produced in a host cell, the composition will typically be an expression vector. In some embodiments, the vector is capable of autonomous replication. In other embodiments, the vector is a viral vector, insect vector, or a bacterial vector. The vector can alternatively be a plasmid, a phage, a cosmid, a mini-chromosome, a virus like particle (VLP), or a virus. Nucleic acid molecules can also be delivered in liposomes or adhered to nanoparticles. Materials and methodology for preparing liposomes and nanoparticles are well-known in the art. The sequence encoding an antibody is operatively linked to a promoter that is active in host cells. There will typically also be a polyA signal sequence, one or more introns, and optionally other control sequences, such as an enhancer. The promoter can be a constitutive promoter, an inducible promoter, or cell-type specific promoter. Such promoters are well known in the art.

The sequence of an antibody is readily determined for a monoclonal antibody. A variety of techniques can be used to clone, identify and sequence the antibody chains. In one technique, primers for the variable regions are used in an amplification reaction. The resulting amplified fragment can be inserted into a vector and grown or sequenced directly. With the sequence of the variable regions of the heavy and light chains, expression vectors can be constructed for scFv, Fv, Fab, and the like.

Antibodies, including monoclonal antibodies, scFv, an F(ab') fragment, an F(ab) fragment and an F(ab')$_2$ fragment, may be coupled to a protein transduction domain (PTD) or other molecule, e.g., polysialic acid, that can facilitate the crossing of the blood brain barrier. Two general classes of PTDs have been described, including positively charged transduction domains (cationic) and protein leader sequence derived domains (hydrophobic). Both are able to transduce wide variety of cell types. The cationic type domain is generally 10 to 30 amino acid residues in length and enriched in basic amino acids, e.g., arginine and lysine. Many PTDs are well-know and have been identified in proteins, such as synB peptide derived from protegrin, Drosophila homeodomain transcription factors antennapedia, HIV-1 transactivating protein TAT, engineered chimeric PTDs. In addition, PTDs may be identified by phage display methods. Sequences of exemplary PTDs include YGRKKRRQRRR (SEQ ID No.9) from HIV tat, MIIYRDLISH (SEQ ID No.10) from human translationally controlled tumor protein (TCTP), RQIKIWFQNRRMKW (SEQ ID No.11) from antennapedia, KLALKLALKALKAALKLA (SEQ ID NO.12), GWTLNSAGYLLGKINLKALAALAKKIL from galanin (SEQ ID NO. 13), GALFLGWLGAAGSTMGAWSQPKKKRKV (SEQ ID NO. 14) from SV40, RGGRLSYSRRRFSTSTGR (SEQ ID NO. 15) and RRLSYSRRRF (SEQ ID NO. 16) from protegrin. Antibodies may be coupled to a PTD as a fusion protein or chemically, using one of well-known methods.

5. Uses of Antibodies

The antibodies may be used for treatment or diagnosis of tauopathies and related diseases. Treatment includes prevention of disease, amelioration of disease or symptoms, and the like. The antibodies may be delivered as protein, as a nucleic acid molecule that encodes the antibodies or via cells (e.g. stem cells) expressing the antibodies. As disclosed herein, the antibodies may be a single chain, double chain, tetramer, or other multimer.

The antibodies may also be used to identify mimotopes of tau, including mimotopes of aggregated tau, which could then be used in a vaccine. A mimotope is a macromolecule, often a peptide, which mimics the structure of an epitope. Because of this property it causes an antibody response similar to the one elicited by the epitope. Briefly, the anti-tau antibodies are used to query a phage display library or other type of peptide library for a peptide that mimics the conformational antigenic determinant in aggregated repeat domain of tau. Such a peptide is a mimotope. The mimotope can be formulated and used as a therapeutic for tauopathies. For a vaccine, a mimotope that is antigenic, but not immunogenic, can be coupled to a carrier. Mimotopes can also be used for generation of antibodies, including polyclonal and monoclonal antibodies and scFv, Fab, recombinant antibodies, chimeric antibodies and the like, that will inhibit aggregation of tau and have a therapeutic effect.

Anti-tau antibodies, including scFv, Fab, Fab' or F(ab)', can be used to raise anti-idiotype antibodies, which are then used as a vaccine. Anti-idiotypic antibody may mimic the original antigen. In one embodiment, anti-idiotype antibodies are monoclonal or scFv, Fab, Fab', F(ab)' and may be generated by recombinant DNA techniques that are well-known in the art.

6. Formulations and Delivery of Antibodies

Humanized, anti-tau antibodies, including scFv, Fab fragment, and Fab'2, may be formulated as a pharmaceutical composition for delivery to a subject (e.g., for use as a passive antibody therapy) or for the generation of an active vaccine to raise anti-idiotypic antibodies mimicking the antigenic determinant of tau. The compositions may include adjuvants and pharmaceutically acceptable excipients.

Anti-tau antibody compositions may comprise a pharmaceutically acceptable excipient, carrier, buffer, stabilizer or other materials well known to those skilled in the art. Such materials should be non-toxic and should not interfere with the efficacy of the active ingredient. The precise nature of the carrier or other material can depend on the route of administration, e.g. intravenous, cutaneous or subcutaneous, nasal, intramuscular, intraperitoneal routes.

For intravenous, intraperitoneal, intrathecal, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilizers, buffers, antioxidants and other additives can be included, as required.

Immunogenic compositions comprise one or more anti-tau antibodies and hybrid antibodies (one antigenic determinant of antibody will bind one epitope and another one will bind another epitope).

The compositions may be packaged as a solution, but can also be packaged in dry form (e.g., desiccated), in which case, a user adds any necessary liquid. Typically, additives such as buffers, stabilizers, preservatives, excipients, carriers, and other non-active ingredients will also be present in the package. Additives are typically pharmaceutically acceptable and bio-compatible.

When antibodies are to be delivered as a DNA composition, the composition will typically be an expression vector. In some embodiments, the vector is capable of autonomous replication. In other embodiments, the vector is a viral vector, insect vector, or a bacterial vector. The vector can alternatively be a plasmid, a phage, a cosmid, a mini-chromosome, a virus like particle (VLP), or a virus. The delivery vehicle can also be a liposome or nanoparticle. The sequence encoding an antibody or will be operatively linked to a promoter that is active in host cells. There will typically also be a polyA signal sequence, one or more introns, and optionally other control sequences, such as an enhancer. The promoter can be a constitutive promoter, an inducible promoter, or cell-type specific promoter. Such promoters are well known in the art.

In addition, the protein or nucleic acid may be presented in separate containers or combined in a single container. A container can be a vial, ampoule, tube, or well of a multi-well device, reservoir, syringe or any other kind of container. The container or containers may be provided as a kit. If one or more of the containers comprises desiccated ingredients the liquids for reconstitution may be provided in the kit as well or provided by the user. The amount of solution in each container or that is added to each container is commensurate with the route of administration and how many doses are in each container. The compositions are generally provided sterile. Typical sterilization methods include filtration, irradiation and gas treatment.

Methods for treatment of tauopathies and related diseases are provided. Methods include administering a therapeutically effective amount of a composition disclosed herein. Administration is preferably in a "therapeutically effective amount" or "prophylactically effective amount" (as the case can be, although prophylaxis can be considered therapy), this being sufficient to show benefit to the individual. Effectiveness may be measured by any number of parameters or endpoints, such as an improvement in cognitive ability, a slowing down of cognitive decline, an improvement of physical abilities or slowing of physical decline, and the like. After the demise of a patient, the amount of neurofibrillary tangles and other symptoms of AD can be directly assessed and used to help guide determination of effective doses. The actual amount administered, and rate and time-course of administration, will depend on the nature and severity of protein aggregation disease being treated. Prescription of treatment, e.g. decisions on dosage etc, is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in Remington's Pharmaceutical Sciences, 16th edition, Osol, A. (ed), 1980. Furthermore, a composition can be administered alone or in combination with other treatments, either simultaneously or sequentially dependent upon the condition to be treated.

The following examples are offered by way of illustration, and not by way of limitation.

EXAMPLES

Example 1

Generation of Anti-Tau Antibodies to N-Terminal Region of Tau

In this example, an exemplary epitope of tau is used to generate antibodies specific to the N-terminal region.

The peptide from residue 2 through 18 of tau was fused with MultiTEP protein, a string of foreign promiscuous Th (helper T cell) epitopes from tetanus toxin TT, HBV and Flu and used to immunize mice. This region of tau is hidden when tau is folded normally, but becomes exposed during aggregation of tau. The MultiTEP activates CD4+ T cells in $H2^{bxs}$ and $H2^b$ (data for production of IFN-γ and IL-4 not shown) mice as well as activates human helper T cells expressing various MHC class II/DR molecules.

Figure 1B:
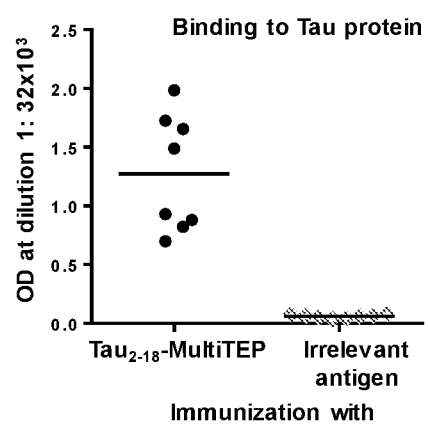
FIG. 1B shows the level of antibody response to full-length tau protein detected in anti-$tau_{2-18}$ immune sera diluted 1:32000. Lines indicate the average of $OD_{450}$ (n=8).
Figure 1C:
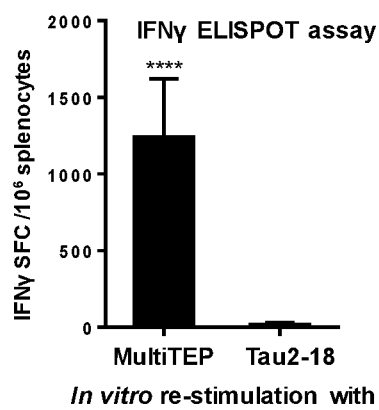
FIG. 1C shows the number of IFN-$\gamma$ producing cells detected in the cultures of immune splenocytes. The number of IFN$\gamma$ producing splenocytes was analysed by ELISPOT assay after ex vivo re-stimulation of cells with 10 µg/ml $tau_{2-18}$ peptide and MultiTEP protein (FIG. 1C) or $tau_{2-18}$-MultiTEP protein (data not shown). Error bars indicate average±s.d. (n=4; $P \leq 0.001$).

B6SJL mice ($H2^{bxs}$ immune haplotype) were immunized with a $tau_{2-18}$-MultiTEP immunogen formulated in the adjuvant Quil A (also known as QS21). Both humoral (ELISA) and cellular (ELISPOT) immune responses were measured. Immunization induced high titers of $tau_{2-18}$-specific antibodies that also recognized 0N/4R full-length tau (FIG. 1A and FIG. 1B). The epitope vaccine also induced a strong T cell response that was specific to MultiTEP, but not $tau_{2-18}$ (FIG. 1C). In conclusion, $tau_{2-18}$-MultiTEP vaccine in QuilA adjuvant produced antibodies specific to various tau proteins and these antibodies can be used for passive vaccination of subjects at various stages of tauopathy (e.g. Alzheimer's disease).

Example 2

Therapeutic Potency of Anti-Tau Antibody

This example shows the functional potency of administering anti-tau antibodies on inhibiting aggregation of tau.

Figure 2:
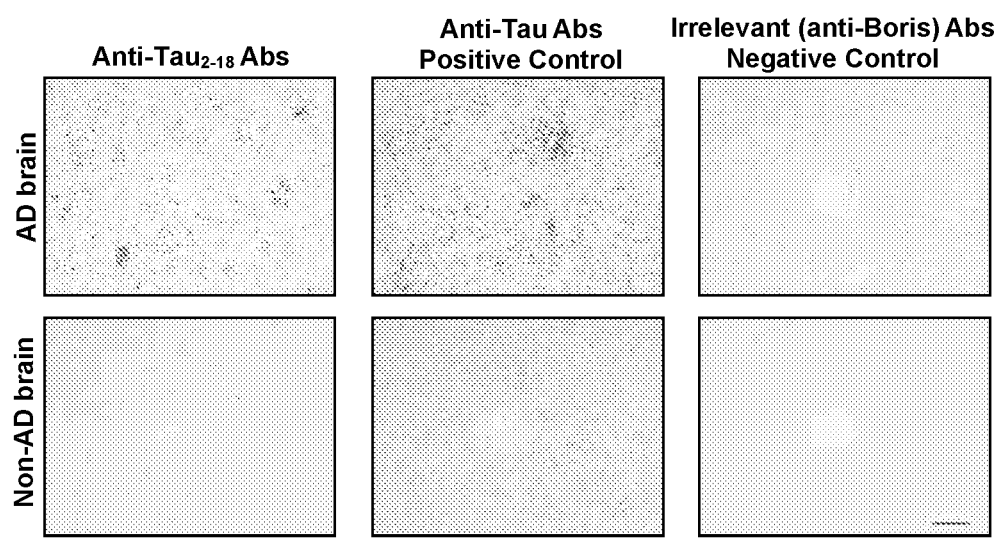
FIG. 2 shows photographs of brain sections stained with anti-$tau_{2-18}$ antibody. Sera from mice immunized with $tau_{2-18}$-MultiTEP and control antisera from mice immunized with an irrelevant antigen were used to stain sections of Alzheimer's Disease (AD) brain and non-AD brain. Original magnifications: 10×, scale bar=100 µm; 20×, scale bar=50 µm.

Sera from experimental mice immunized with the epitope vaccine and control animals immunized with an irrelevant antigen were tested on brain sections from AD and non-AD cases. FIG. 2 shows that immune sera at a dilution 1:500 from experimental, but not control mice recognized neurofibrillary tangles (NFT) in brain from an AD patient (Tangle stage V, Plaque stage C). Importantly, the same immune sera did not bind tau in the brain sections from non-AD case. Thus, antibodies generated after immunization of tau antigen vaccines are specific to the only pathological form of tau.

Moreover, anti-$tau_{2-18}$ antibodies purified from the sera of vaccinated mice were tested for their ability to inhibit cell-to-cell propagation of tau aggregates, using the method of Kfoury et al. (Kfoury, N. et al., J Biol Chem 2012, 287, 19440-19451).

The antibodies were able to inhibit cell-cell progapation of both full-length tau and repeat domain (RD) aggregates, evidencing the therapeutic benefit of these antibodies.

Figure 3:
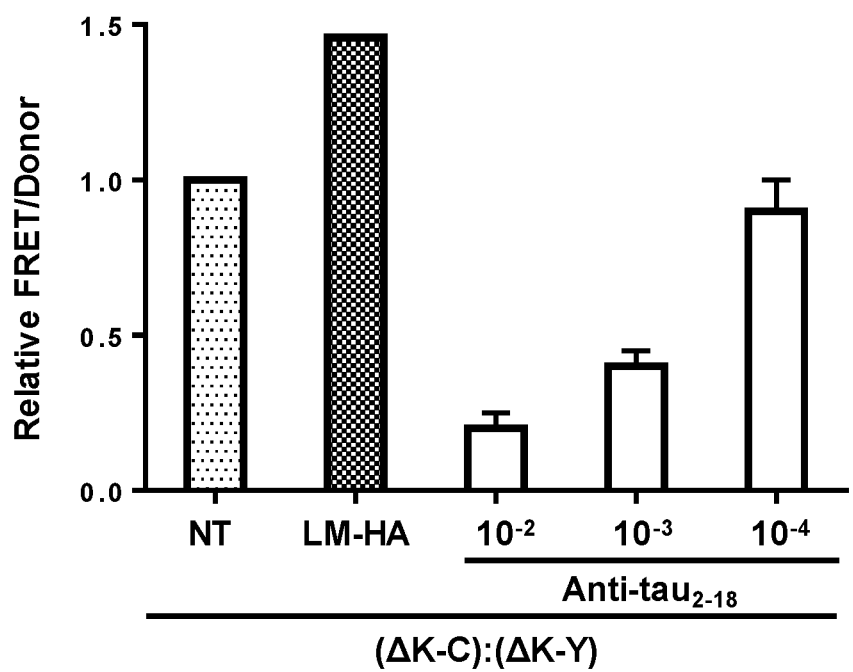
FIGS. 3 shows efficacy of anti-$tau_{2-18}$ antibody detected in ex vivo model system.

More specifically, trans-cellular movement of aggregated tau was assessed in HEK293 cells transfected with tau repeat domain (RD) containing a deletion of lysine at position 280 (ΔK280) and fused to cyan or yellow fluorescent protein (RD-CFP) or (RD-YFP) (ΔK-C):(ΔK-Y). A second population of HEK293 cells was transfected with hemagglutinin-tagged tau (RD) containing two disease-associated mutations that increase aggregation: P301L and V337M (LM) (LM-HA). When the two cell populations were co-cultured, trans-cellular propagation of LM-HA aggregates from donor cells (HEK293 cells transfected with LM-HA) induces aggregation of ΔK-C:ΔK-Y in recipient cells (HEK293 transfected with RD-CFP/RD-YFP) as detected by fluorescence resonance energy transfer (FRET) between CFP and YFP, which yields a signal detected by a fluorescence plate reader. To measure baseline endogenous aggregation, a (ΔK-C):(ΔK-Y) cell population was co-cultured with mock-transfected cells (NT). To test the ability of antibodies purified from sera to block cell-to-cell transfer of RD aggregates, anti-$tau_{2-18}$ antibody (0.4 mg/ml) was added to the culture at different dilutions ($10^{-2}$, $10^{-3}$ and $10^{-4}$) and incubated for 48 h. A dose-dependent reduction of FRET signal, indicating reduced transcellular propagation of LM-HA aggregates, is observed with anti-$tau_{2-18}$ (FIG. 3), whereas nonspecific IgG had no effect (data not shown). Because the $tau_{2-18}$ peptide is localized outside of the RD region, these data indicate that anti-$tau_{2-18}$ antibody recognizes a conformational antigenic determinant (mimotope(s)) in aggregated RD and blocks its cell-to-cell propagation. To show possible binding of anti-$tau_{2-18}$ to RD aggregates, HEK293 cells were transfected with RD(ΔK)-YFP or were mock-transfected (NT). Anti-$tau_{2-18}$ antibody was added to the culture medium for 48 h. Cells were fixed, permeabilized, and stained with an anti-mouse secondary antibody labeled with Alexa 546 and analyzed by confocal microscopy. Anti-$tau_{2-18}$/RDΔ(K)-YFP complexes were identified when RDΔ(K)-YFP is expressed but not in its absence (NT) (data not shown).

Figure 4:
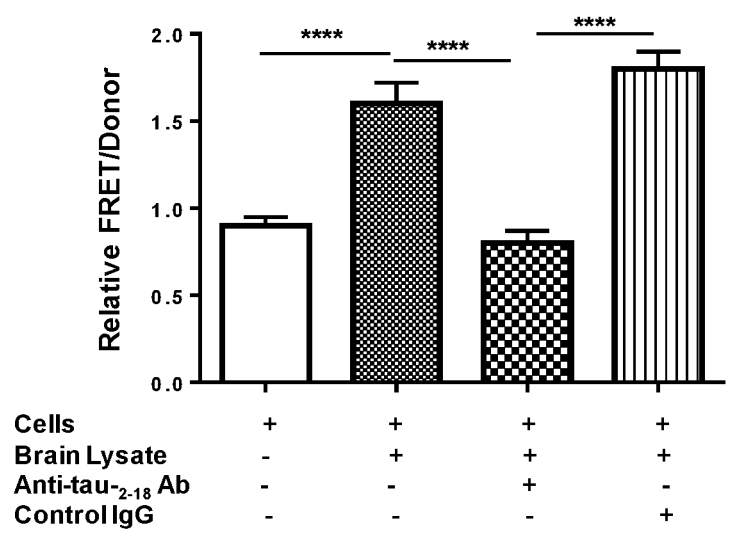
FIGS. 4 shows a graph of FRET analysis of anti-$tau_{2-18}$ antibody used to block the ability of brain lysate from transgenic mice to induce aggregation of intracellular repeat domain (RD). Brain lysate was either untreated or treated with anti-$tau_{2-18}$ antibody or irrelevant control IgG and added to HEK293 cells co-transfected with RD($\Delta$K)-CFP and RD($\Delta$K)-YFP prior to FRET analysis. Increased FRET signal was detected in wells with untreated brain lysate or treated with irrelevant control IgG brain lysate. Treatment of lysate with anti-$tau_{2-18}$ antibody decreased FRET signal due to blocking the full-length tau in brain lysate and inhibition of induction of RD aggregation.

In another set of experiments, the ability of anti-$tau_{2-18}$ antibody was tested for ability to block full-length tau aggregates from entering a cell and inducing aggregation of intracellular RD. The experiment was designed as described above except that the aggregation ΔK-C:ΔK-Y in recipient cells was induced by adding aggregated tau from brain lysates of P301S Tg (transgenic) mice that were either untreated or pre-incubated with anti-$tau_{2-18}$ antibody. As expected, addition of untreated brain lysate increased a FRET signal, whereas pre-treating of brain lysate with anti-$tau_{2-18}$ antibody completely blocked the ability of brain lysate to induce the aggregation of RD in recipient cells (FIG. 4). Importantly, using confocal microscopy brain lysate/anti-$tau_{2-18}$ antibody complexes are shown to internalize into the RD-YFP transfected cells, but not in control mock-transfected cells (NT) with added brain lysates from Tg mice. Of course, antibodies were not detected in NT cells or in RD-YFP cells when tau aggregates from Tg mice were not added to the test tubes (data not shown).

This shows that therapeutic anti-tau antibodies can be generated with a non-phosphorylated tau molecules or their derivatives (e.g. B cell epitopes). Indeed, non-phosphorylated tau may be used for generation of therapeutic antibodies that will be safe to administrate to subjects with tauopathy, because such antibodies will not get inside normal cells and inhibit function of normal tau molecules.

Example 3

Generation and Characterization of Monoclonal Anti-Tau Antibodies

In this example, monoclonal mouse anti-tau antibodies are generated and characterized.

Anti-tau$_{2-18}$ monoclonal antibodies were generated using well-known hybridoma technology. ELISA assays identified several clones producing antibody that bound recombinant human tau protein.

Figure 5:
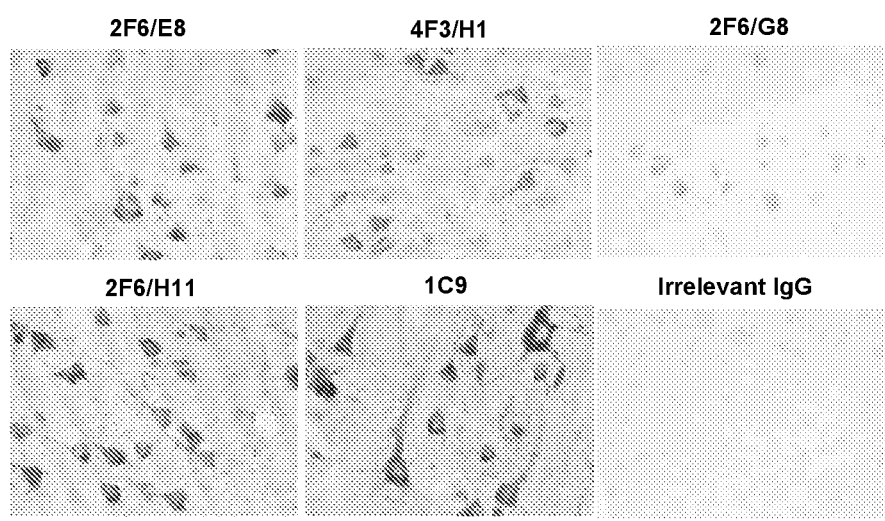
FIG. 5 shows photographs of brain sections stained with anti-$tau_{2-18}$ monoclonal antibodies (2F6/E8, 2F6/H11, 4F3/H1, 1C9 and 2F6/G8) and control mouse IgG. Concentration of antibodies is 1 µg/ml. Original magnifications: 40×.

Antibodies were purified from five selected clones. Their therapeutic efficacy was assessed by binding to pathological tau in brain sections from AD cases. FIG. 5 shows that all five selected antibodies, but not the irrelevant control IgG, recognized neurofibrillary tangles (NFT) in brain sections from an AD patient. The intensity of staining differs among the antibodies, suggesting that the monoclonal antibodies have varying affinity of binding. 2F6/G8 binding to pathological Tau brain sections was too weak, therefore it was excluded from further testing.

Figures 6A, 6B:
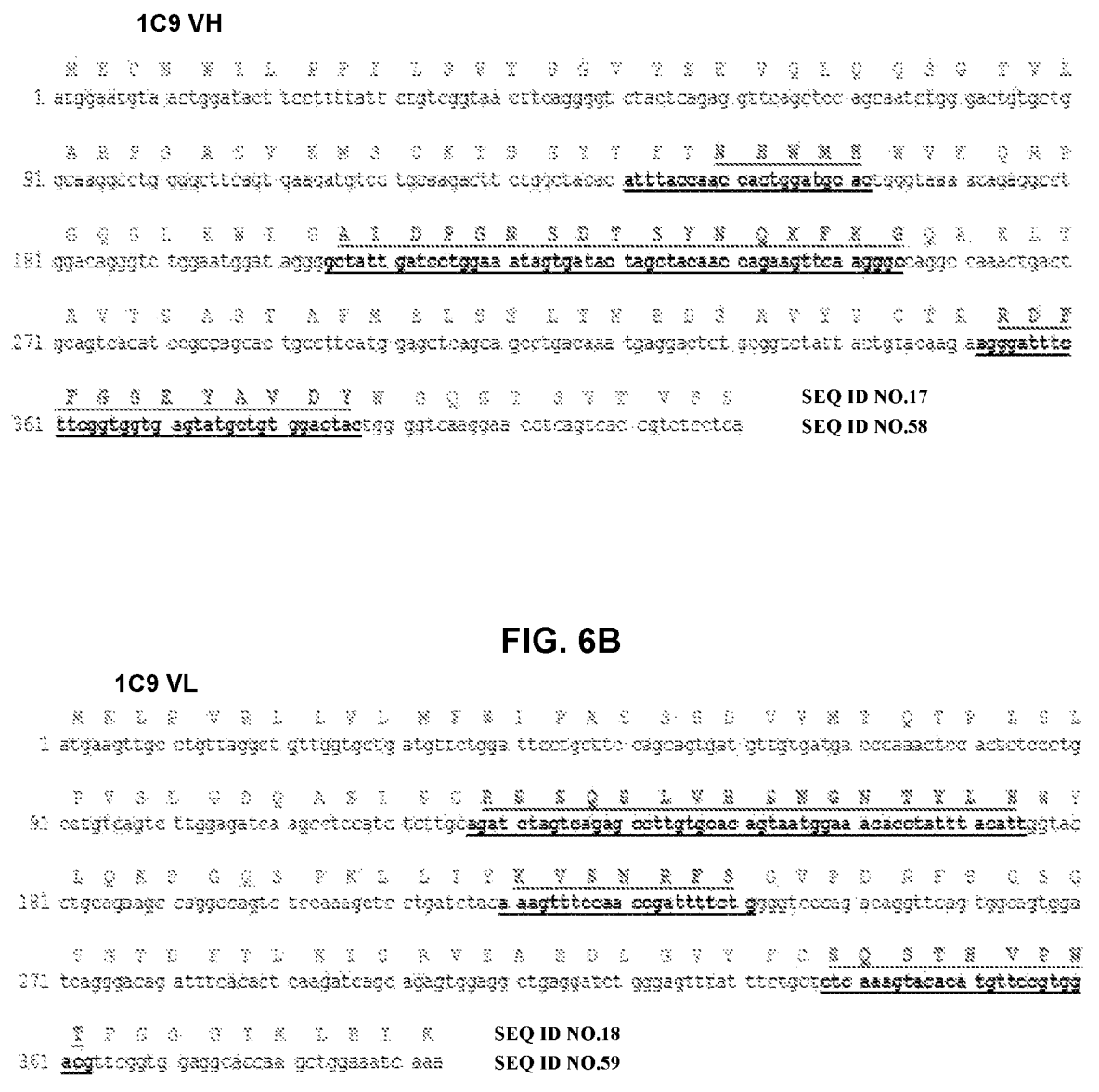

The fine specificity of monoclonal antibodies was mapped by alanine scanning. More specifically, a series of peptides was constructed in which successive amino acids in the tau$_{2-18}$ peptide was substituted by alanine, resulting in 18 peptides, each of which differs from tau$_{2-18}$ by one amino acid. Alanines in the original peptide were replaced by serine. The data showed that antibodies recognized either $_4$PXQEF$_8$ or $_4$PXQEXE$_9$ in the tau$_{2-18}$ peptide. The X indicates that the amino acid at that position did not affect binding of the antibody. Amino acid sequences for variable regions of selected clones, 1C9, 4F3/H1, and 2F6/H11, are presented in FIGS. 6-8 and as SEQ ID Nos: 17-22. The amino acid sequences of the CDR regions are presented in FIG. 6 and as SEQ ID Nos:23-28 for 1C9, FIG. 7 and SEQ ID Nos: 29-34 for 4F3/H1 and FIG. 8 and SEQ ID Nos:35-37 for 2F6/H11. The amino acid sequences of CDRs from clone 2F6/E8 were the same as 2F6/H11 as well as CDRs of 2F6/H11 VL region were the same as CDRs of 1C9 VL region.

Example 4

Murine Monoclonal Antibody Selectively Recognized Pathological Tau in Brain Extracts from AD Cases One of the murine monoclonal antibodies, 1C9 was chosen for further analyses. Specificity testing showed that this novel antibody recognized full-length recombinant tau, but not tau that lacks tau$_{2-18}$ domain in western blot (FIG. 9A). 1C9 mAb bound different forms of recombinant tau: monomeric, oligomeric and fibrillar tau in dot blot assay (FIG. 9B). 1C9 mAb recognized pathological tau (both neuropil threads and NFT) in the fixed brain sections from AD cases (FIG. 9C), but did not bind to the brain sections from a non-AD subject.

In denaturing conditions of western blot 1C9 bound different forms of tau in homogenates of postmortem AD and control brains (FIG. 9D) showing typical pattern as in case of HT7 antibodies recognizing total tau. In contrast, in non-denaturing dot blot assay 1C9 selectively bound to soluble fraction of postmortem AD brain extracts (FIG. 9E) indicating that PAD is more exposed and accessible in the AD brains as opposed to controls.

Example 5

Humanization of Monoclonal Anti-Tau Antibodies

One of the murine monoclonal antibodies, 1C9, was chosen and humanized.

Figure 10A:
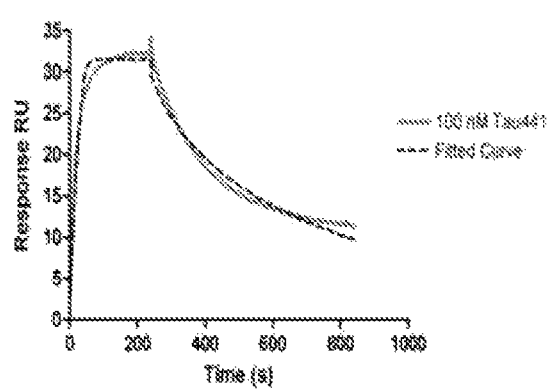
FIG. 10 shows the affinity of binding of 1C9 mouse monoclonal antibody (FIG. 10A) and its chimeric humanized version (FIG. 10B) with recombinant tau protein determined by Biacore analysis.
Figure 10B:
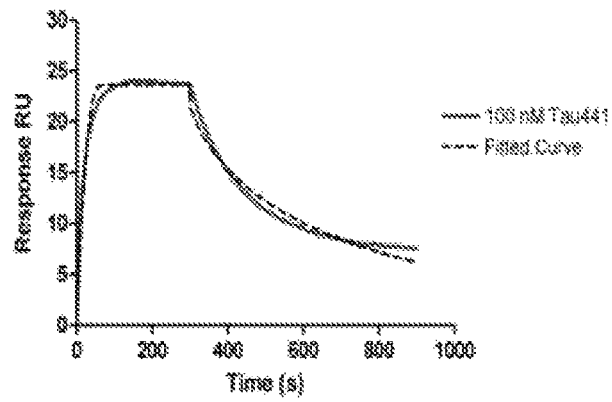

The 1C9 antibody was first partially humanized by replacement of the mouse Fc fragment with a human IgG1 Fc fragment. The binding affinity of this chimeric humanized antibody to recombinant tau protein was determined by surface plasmon resonance (SPR) analysis. Data obtained showed that conversion of mouse mAb to chimeric mAb did not affect the affinity of binding (FIG. 10).

The 1C9 chimeric antibody was further humanized by replacing the heavy and light chain frameworks with human frameworks. The human FR1, FR2, FR3, which share the highest identities with those of the mouse antibody were selected and assembled with mouse CDRs (SEQ ID Nos: 23-25 for the heavy chain CDRs and SEQ ID Nos: 26-28 for the light chain CDRs) using overlapping PCR. Amplified fragments were inserted into a phage display vector to create a library of phage expressing humanized Fab fragments. Strong binders to recombinant tau protein were selected after three rounds of panning. Affinity ranking of selected antibody was assessed with an Octet system (fortéBIO, Pall Corporation).

Figure 11:
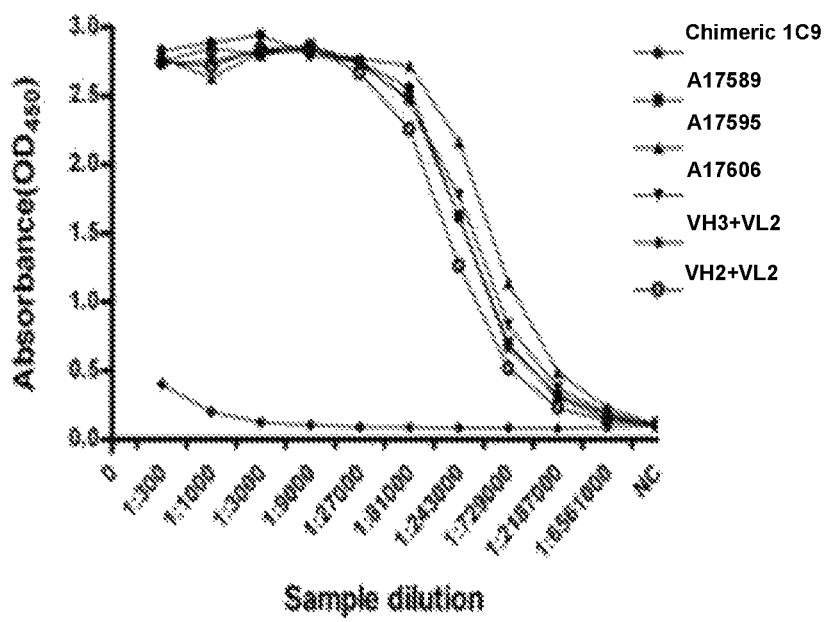
FIG. 11 presents binding validation of selected top ten humanized antibodies by ELISA. ELISA plates were coated with recombinant tau protein and incubated with different dilutions of each antibody followed by incubation with anti-human IgG secondary antibody conjugated with HRP.

Several phage clones were selected for DNA sequence analysis and further testing. The VH and VL protein sequences of eight clones are presented as SEQ ID Nos: 38-53. DNA encoding the Fab VH and VL from the five clones having the highest affinity was used in construction of IgG antibodies. Purified antibodies were analyzed by ELISA (FIG. 11). For ELISA, 96-well plates were coated with recombinant tau protein and incubated with different dilutions of each antibody followed by incubation with an anti-human IgG secondary antibody conjugated with HRP (horse radish peroxidase). The reaction was developed by adding 3,3',5,5'tetramethylbenzidine (TMB) substrate solution and stopped with 2 M $H_2SO_4$. The optical density (OD) was read at 450 nm. Four humanized antibodies demonstrated binding to tau protein and had similar titers to a chimeric version of the parent antibody 1C9 (FIG. 11).

Figure 12:
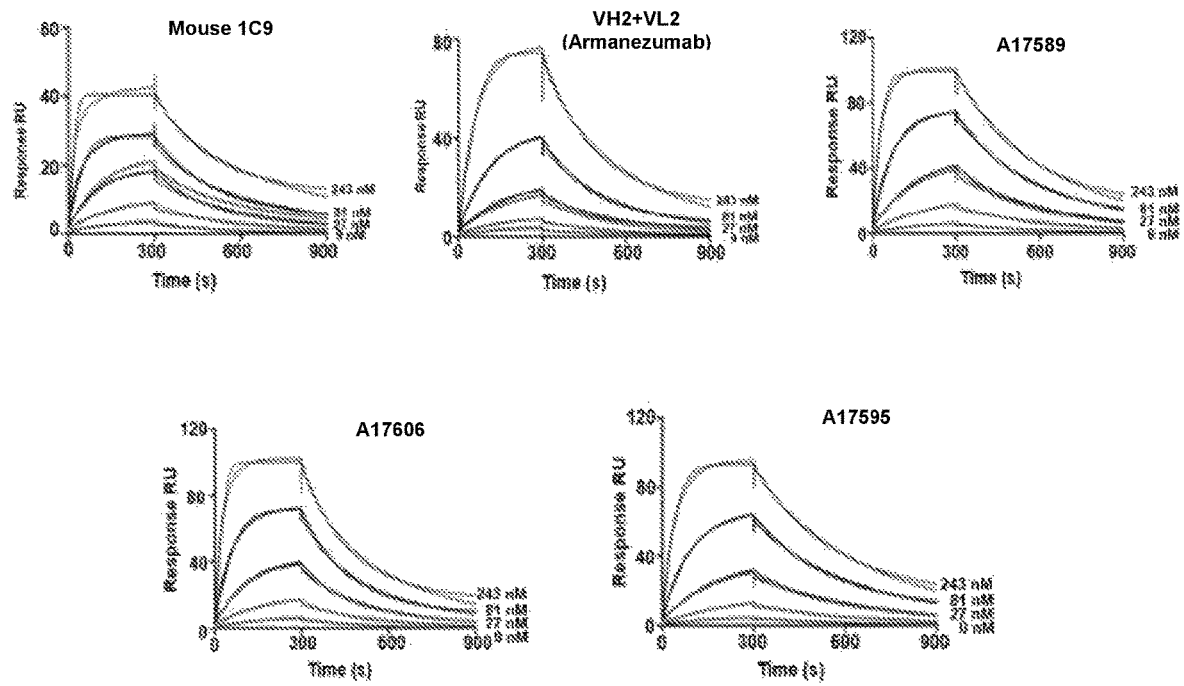
FIG. 12 presents affinity of binding of different clones of fully humanized antibodies and the parental mouse antibody with recombinant tau protein determined by Biacore.

Affinity of the humanized antibodies was determined by SPR (Biacore) analysis (FIG. 12). All humanized antibodies retain $K_D$ of parental mouse MoAb. One of them was selected (based on binding to brain sections from AD case) and designated as Armanezumab. Protein and DNA sequences of four selected antibodies including Armanezumab are presented in FIGS. 13-17. Armanezumab VH/CH and VL/CL sequence is presented in SEQ ID Nos:54-55 for amino acid sequences and SEQ ID Nos: 56-57 for nucleotide sequences.

Example 6

Therapeutic Efficacy of Armanezumab

In this example, therapeutic efficacy of Armanezumab is assessed by several assays, including binding to pathological tau, inhibition of tau cytotoxicity, inhibition of seeding activity, and reduction of tau aggregates in brain.

Figure 18A:
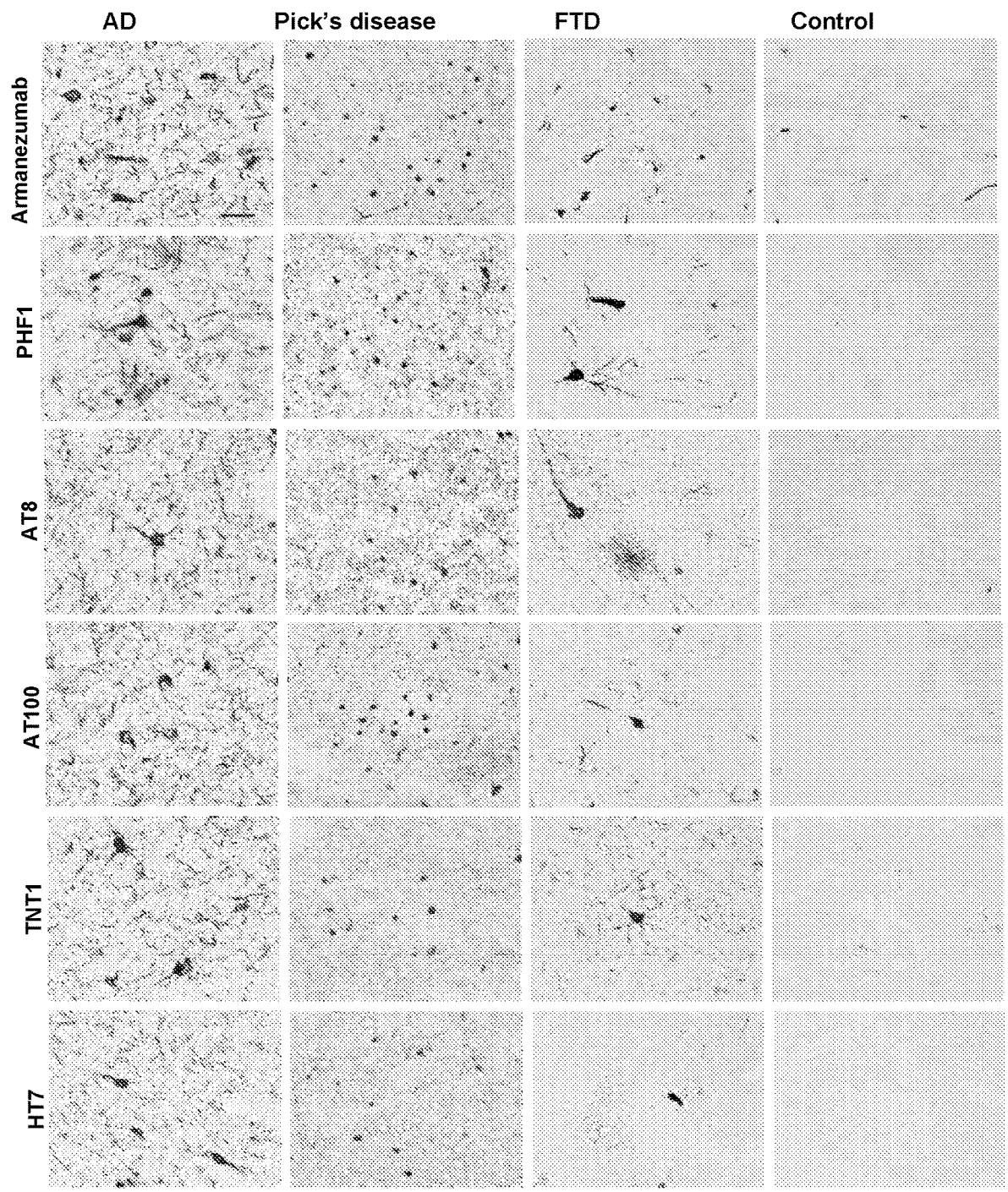
FIG. 18A shows that Armanezumab binds to brain sections form AD, FTD, Pick's disease cases. No binding had been seen with brain section with no tauopathy. Binding of commercial anti-tau antibodies of different specificities (PHF1, AT8, AT100, TNT1, HT7) to the adjacent sections have been also shown for comparison.

Binding of Armanezumab to pathological tau. The activity of Armanezumab was tested initially by binding to pathological tau in brain sections from AD cases. FIG. 18A shows that Armanezumab recognized pathological tau in brain sections from not only AD cases, but also with pathological tau in brains from frontotemporal lobar dementia (FTLD) and Pick disease cases (tissue obtained from the Brain Bank and Tissue Repository, MIND, UC Irvine). No binding was observed with brain section from control subject without tauopathy. Binding of Armanezumab is very similar to that seen with antibodies of various specificity recognizing pathological tau in tauopathy brains.

Figure 18B:
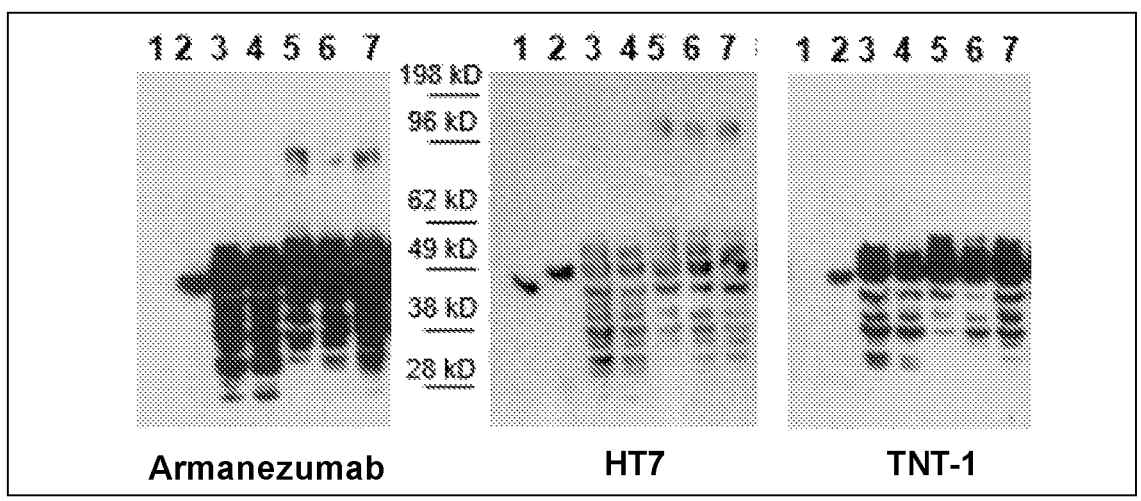
FIG. 18B shows that Armanezumab recognized aggregated forms of tau in brain homogenates from AD cases (Braak stage VI). HT7 recognizing total tau and TNT-1 specific to N-terminus of tau were used as positive controls.

Data in FIG. 18B shows that like 1C9, Armanezumab bound to full-length recombinant tau, monomeric and aggregated forms of tau in AD brain extracts and did not recognize recombinant tauΔ2-18 (FIG. 18B). It labels the similar pattern of tau protein as HT7 recognizing total tau. In contrast to commercial PAD-specific antibody TNT-1, Armanezumab bound also the aggregated forms of tau in brain extracts from AD patients.

Figure 19A:
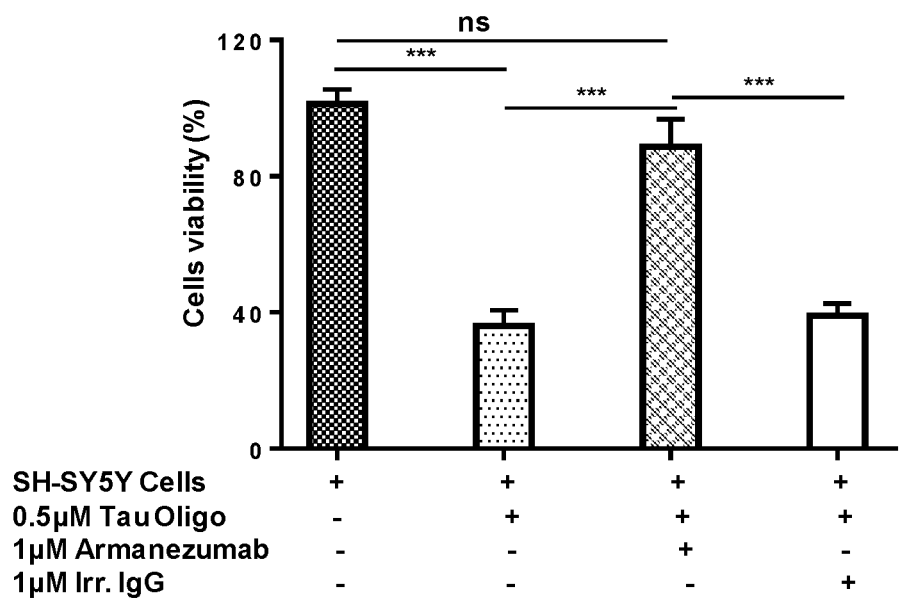
FIG. 19 shows that Armanezumab inhibited neurotoxic effect of tau oligomers on human neuroblastoma SH-SY5Y cells (FIG. 19A) and mouse primary neurons (FIG. 19B).
Figure 19B:
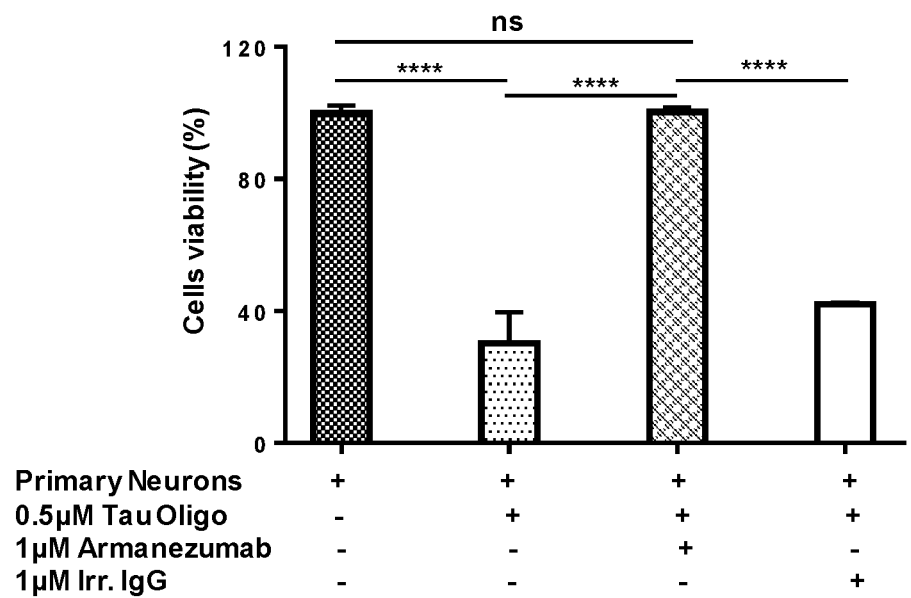

Inhibition of cytotoxicity of tau in vitro. The ability of Armanezumab to inhibit cytotoxicity of tau oligomers was tested in vitro using SH-SY5Y human neuroblastoma cells and mouse primary neurons. Cells were incubated with toxic concentrations (0.5 µM) of tau oligomers and either 1 µM Armanezumab or 1 µM irrelevant IgG antibody. Controls included cells alone and cells incubated with tau oligomers. Cell viability was assayed in all cultures using the 3-(4,5-dimethylthiazol-2-yl)-2,5-diphenyltetrazolium bromide assay. Data were collected (four replicates) and expressed as percentages of control±s.d. As shown in FIG. 19, both, SH-SY5Y human neuroblastoma cells (FIG. 19A) and mouse primary neurons (FIG. 19B) treated with tau oligomers had significantly higher viability when incubated with Armanezumab than when incubated with an irrelevant antibody, which didn't improve viability at all. Furthermore, the viability with Armanezumab was comparable to viability of cells alone.

Figure 20A:
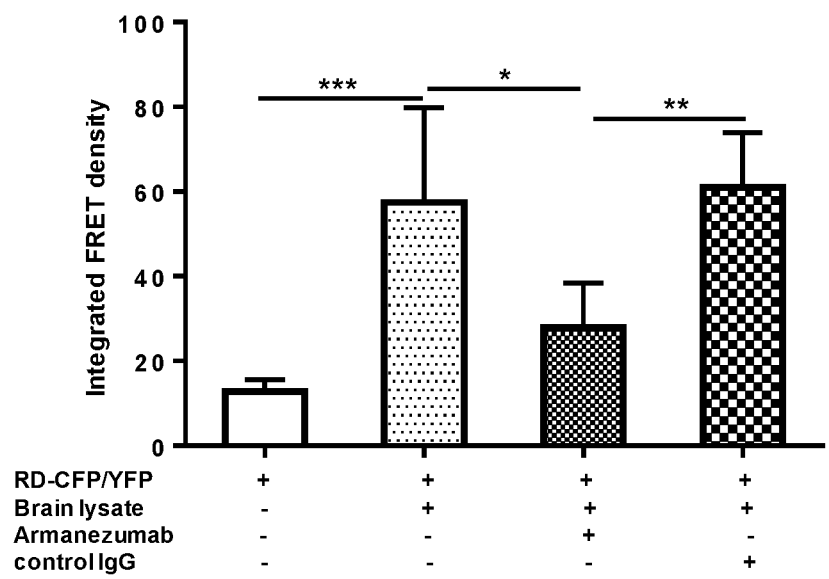
FIG. 20A shows that Armanezumab (10 μg/ml) inhibited the ability of pathological tau in brain lysate of tau (P301S)/Tg mice to induce the aggregation of RD-CFP/RD-YFP in transiently transfected HEK293 cells.

Armanezumab Inhibits seeding activity of aggregated tau: To assess a relevant therapeutic activity of Armanezumab we used high throughput screening test developed in the laboratory of Dr. Diamond as described in Example 2 with small modifications. Aggregation rate in HEK293 cells transiently cotransfected with RD(ΔK)-CFP and RD(ΔK)-YFP (Kfoury, N. et al., J Biol Chem 2012, 287, 19440-19451; Furman J. L. et al., J Vis Exp, 2015, 106, e53205) was tracked by FRET. More vigorous aggregation resulted higher FRET signal could be induced by adding brain lysate from P301S Tg mice containing full-length tau aggregates to the culture of co-transfected cells. We tested the ability of Armanezumab to inhibit this brain lysate induction of intracellular RD(ΔK) aggregation. As shown in FIG. 20A, addition of untreated brain lysate of P301S Tg mice to the transiently transfected cells expressing RD(ΔK)-CFP/YFP increased the number of FRET-positive cells, whereas pretreating brain lysate with Armanezumab inhibited such induction. Interestingly, the number of FRET-positive cells is even lower than background level in samples without induction (FIG. 20A).

Figure 20B:
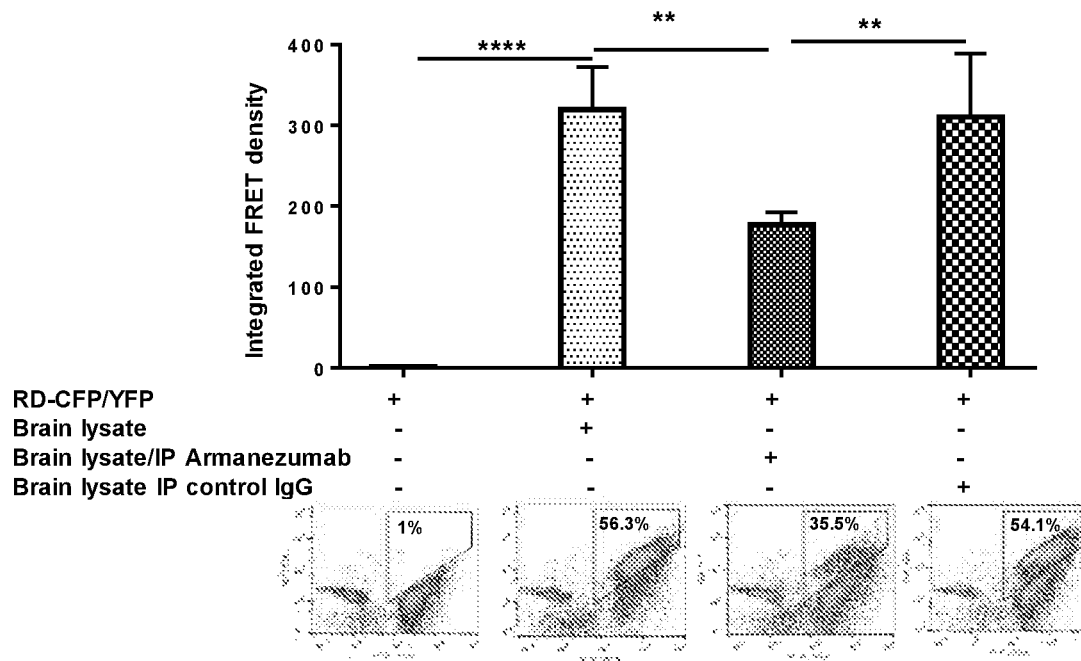
FIG. 20B shows that Armanezumab/protein A/G complex bound and removed pathological tau from brain lysate of tau(P301S)/Tg mice significantly decreasing the ability of lysate to induce the aggregation of RD-CFP/RD-YFP in stably transfected HEK293 cells. Representative FACS images for each group are presented. Numbers indicate the percentage of gated FRET-positive cells.

Armanezumab immunoprecipitates aggregated Tau and inhibits seeding activity of brain lysate from Tau P301S Tg mice. Immunoprecipitation of aggregated Tau from brain lysate of P301S Tau/Tg mice with Armanezumab/protein complex abrogated the ability of brain lysate to induce aggregation of RD(ΔK)-CFP/YFP in HEK293 cells stably transfected with plasmids expressing RD(ΔK)-CFP and RD(ΔK)-YFP. As shown in FIG. 20B, in the absence of a seeding aggregated tau, RD(ΔK)-CFP and RD(ΔK)-YFP did not form aggregates, and only the background signal is observed in FRET. Adding the brain lysates from tau/Tg mice induced aggregation and increased the FRET signal. Immunoprecipitation (IP) of tau aggregates from brain lysate with Armanezumab (50 µg)/Protein A/G complex inhibited the induction of RD(ΔK)-YFP and RD(ΔK)-CFP aggregation and significantly decreased the percentage of FRET-positive cells analyzed by flow cytometry. In contrast, IP of brain lysates with control IgG did not affect the aggregation level. Representative FACS images for each group are presented. Numbers indicate the percentage of gated FRET-positive cells (FIG. 20B).

Reduction of tau-aggregates in the brains of tau/tg mice. The therapeutic efficacy of Armanezumab was also tested in vivo after unilateral injections of 2 µg Armanezumab or control IgG into the hippocampus of 6-8 mo old tau/Tg mice. By this age these mice exhibit substantial tau accumulation and hyperphosphorylation. Five days after a single unilateral stereotactic injection of antibodies, mice (n=7) were perfused and sections examined with different anti-human Tau antibodies.

Figure 21:
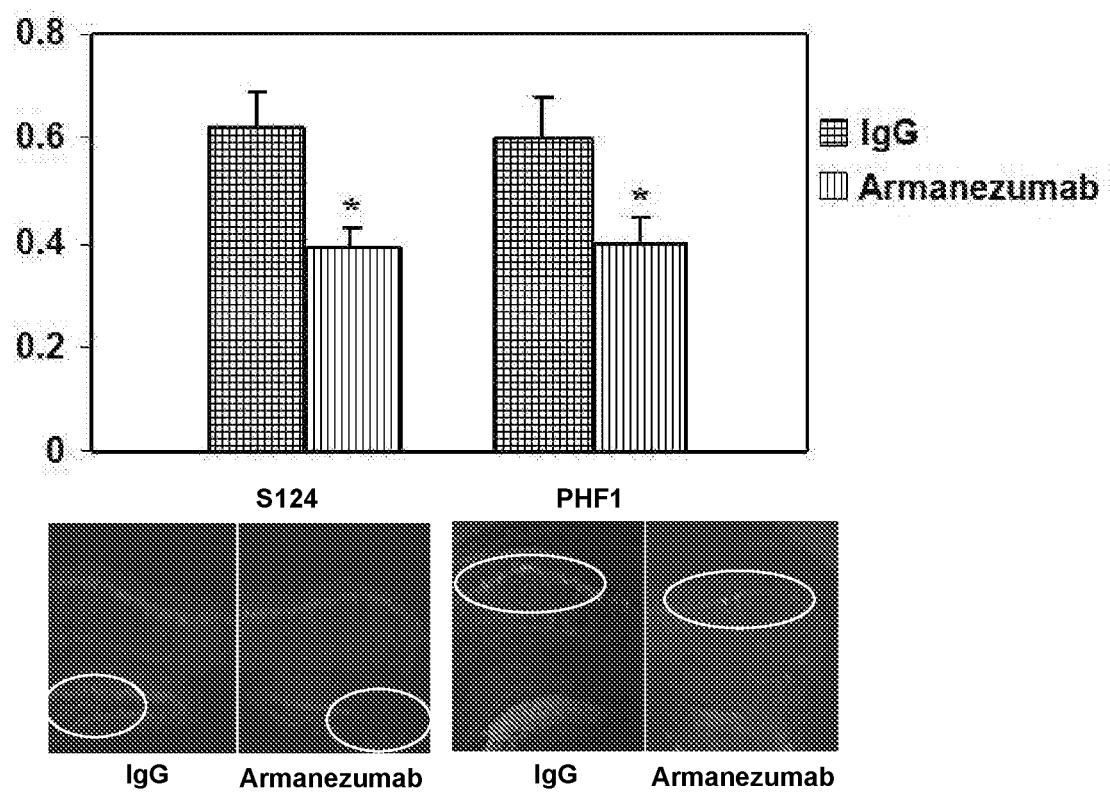
FIG. 21 shows that intracranial injection of Armanezumab into hippocampus of Tau/Tg mice (n=7) reduced tau recognized by antibodies specific to tau phosphorylated at position S214 and to tau phosphorylated at positions S396/S404 (PHF1) compared with control IgG analyzed by confocal microscopy.

As shown in FIG. 21, analyses by confocal microscopy revealed a significant reduction in tau phosphorylated at S214 and tau phosphorylated at S396/S404 (PHF1 tau) on the side injected with Armanezumab as compared to the side injected with control IgG (n=7).

Figure 22:
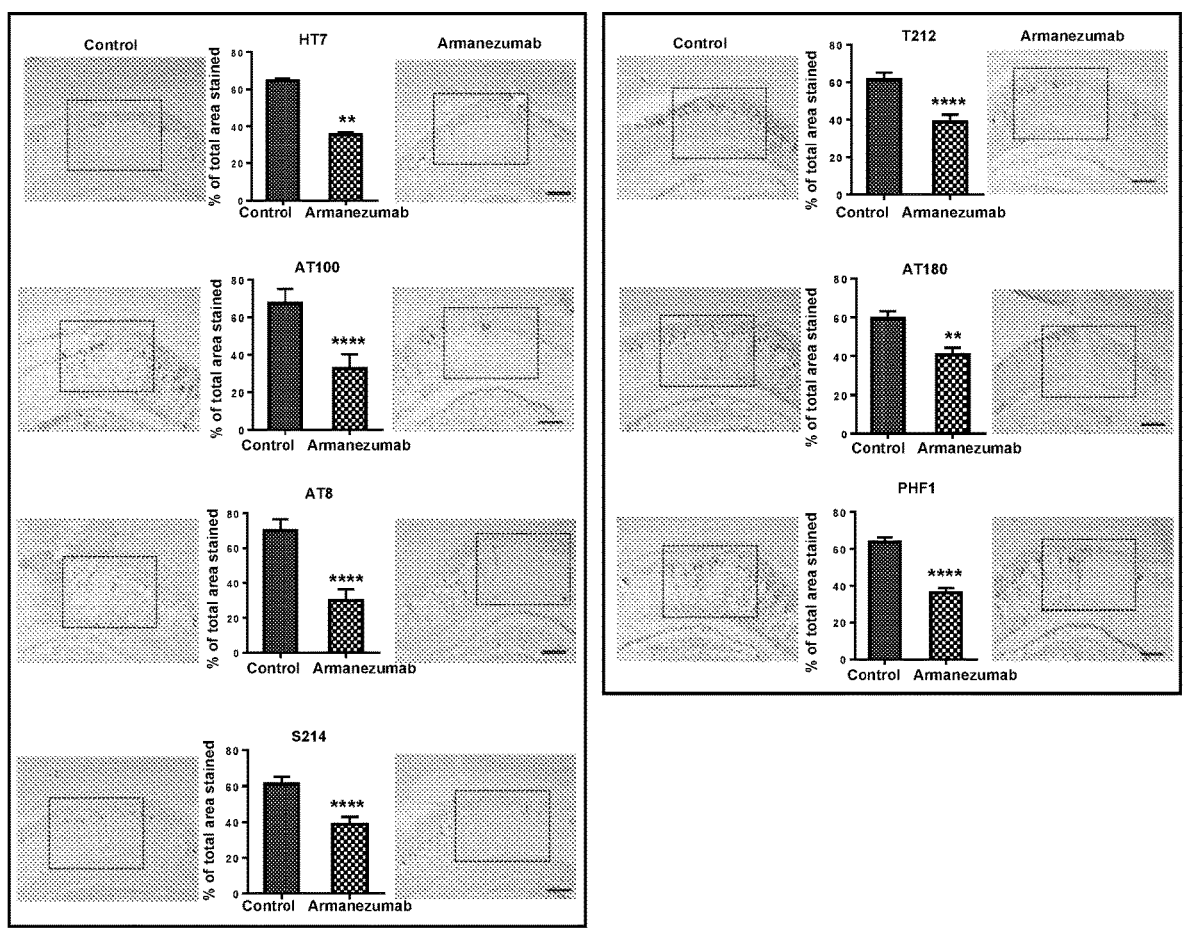
FIG. 22 shows that intracranial injection of Armanezumab into hippocampus of Tau/Tg mice (n=7) reduced tau recognized by antibodies specific to total tau (HT7), tau phosphorylated at positions Thr212 (T212), Ser214 (S214), T212/S214 (AT100), S396/S404 (PHF1), S202/T205 (AT8) and Thr231 (AT180) compared with control IgG analyzed by IHC. Density is expressed in the percentage units calculated by formula $I/(I+C) \times 100$ and $C/(I+C) \times 100$ where I-ipsilateral (Armanezumab injected), C-contralateral (control IgG injected). Average and standard deviation for each hemisphere between all mice were calculated and compared. Representative images for each antibody-injected group are presented (magnification 10×).

In addition, IHC analyses showed reduction of total tau (HT7), phosphorylated tau positive to ATB, pT212, pS214, PHF1, AT100 (S212/S214), AT180. Representative images of brain sections from each antibody staining group is presented in FIG. 22.

Figure 23A:
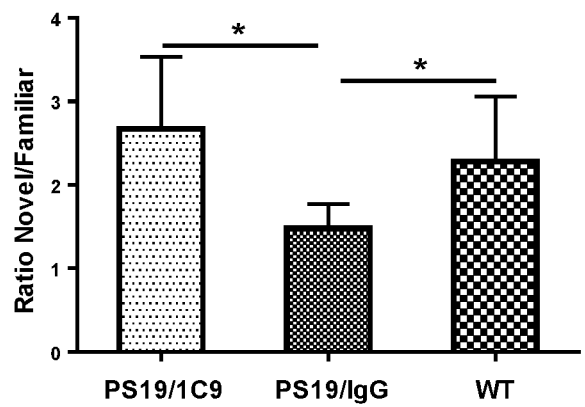
FIG. 23A shows that 1C9 treated tau/Tg mice spent significantly more time with the novel object when compared to IgG treated tau/Tg mice.
Figure 23B:
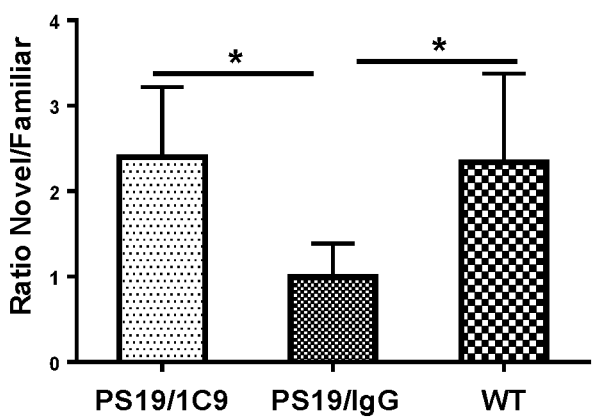
FIG. 23B shows that 1C9 treated tau/Tg mice spent significantly more time within the novel arm when compared to IgG treated tau/Tg mice.

Improvement of recognition memory of tau/Tg mice. To evaluate the in vivo efficacy of Armanezumab, 1C9 moAb, the mouse counterpart of Armanezumab was used for passive vaccination. 3 mo old PS19 tau/Tg mice have been i.p. injected with 250 µg 1C9 weekly until the age of 8-9 mo old. Cognitive improvement was evaluated by Novel Object Recognition (NOR) and Novel Place Recognition (NPR) tests. As shown in FIG. 23, mice treated with 1C9 (n=9) spent significantly more time with novel object (FIG. 23A) as well as within the novel arm (FIG. 23B) when compared to IgG treated tau/Tg mice (n=10).

Example 7

Pharmacokinetics of Armanezumab in Mice and Development of Industrial Cell Line

Figure 24:
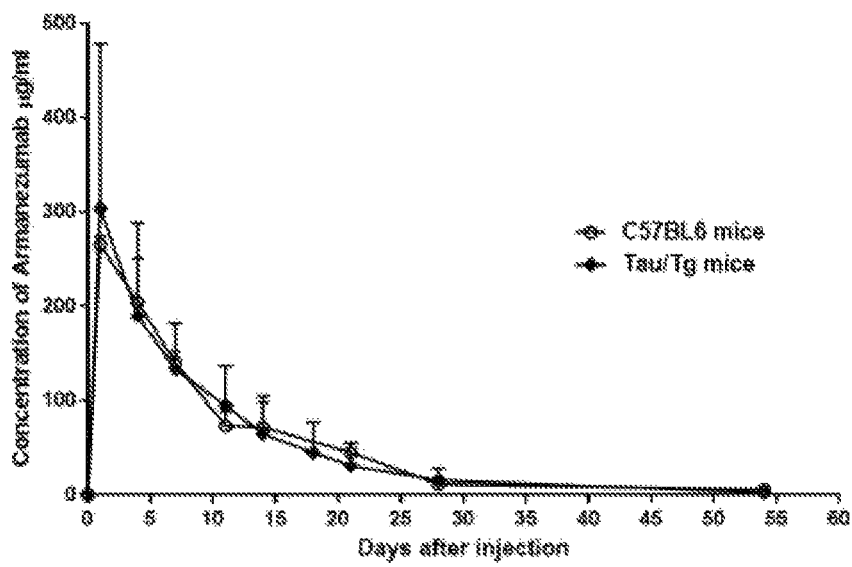
FIG. 24 shows pharmacokinetic analyses of Armanezumab in wildtype mice, in the absence of target-mediated clearance and in Tg mouse model expressing human tau.

PK analyses of Armanezumab in wildtype mice, in the absence of target-mediated clearance and in Tg mouse model expressing human tau, was conducted after the administration of a single dose of Armanezumab via IV bolus injection to C57BL6 and PS19 tau/Tg mice. The concentration of Armanezumab was monitored from day 1 through day 54 following the injection. No differences were observed in the serum concentration x time profiles of Armanezumab in WT and PS19 mice (FIG. 24). In both strains the peak plasma concentration ($C_{max}$) of Armanezumab was observed at day 1, and the average elimination half-life is 9 days (Table in FIG. 24). The rate at which Armanezumab is removed from the system [Elimination rate ($K_{e1}$) constant and the estimated clearance (CL)] also did not differ between strains indicating that the elimination was not target-mediated. The apparent volume of distribution is 2.93 and 2.70 in Tg and wild-type mice, respectively, indicating that Armanezumab was mostly distributed in blood in both strains of mice.

Based on data generated in the studies described above, a stable CHO-DG44 cell line expressing quantities of Armanezumab amenable to scale-up production (1.5 g/L), was developed using MTX amplification.

From the foregoing, it will be appreciated that, although specific embodiments have been described herein for purposes of illustration, various modifications may be made without deviating from the spirit and scope of the invention. Accordingly, the invention is not limited except as by the appended claims.

We claim:

1. A method of treating tauopathy in an individual, the method comprising administrating to the subject a pharmaceutical composition comprising:
   a. a pharmaceutically acceptable excipient suitable for administration to human and
   b. a humanized anti-tau antibody that comprises:
   (i) a VH CDR1 comprising the amino acid sequence of SEQ ID No: 23 and
   a VH CDR2 comprising the amino acid sequence of SEQ ID No: 24 and
   a VH CDR3 comprising the amino acid sequence of SEQ ID No: 25 and
   a VL CDR1 comprising the amino acid sequence of SEQ ID No: 26 and
   a VL CDR2 comprising the amino acid sequence of SEQ ID No: 27 and
   a VL CDR3 comprising the amino acid sequence of SEQ ID No: 28;
   Or
   (ii) a VH CDR1 comprising the amino acid sequence of SEQ ID No: 29 and a VH CDR2 comprising the amino acid sequence of SEQ ID No: 30 and a VH CDR3 comprising the amino acid sequence of SEQ ID No: 31 and a VL CDR1 comprising the amino acid sequence of SEQ ID No: 32 and a VL CDR2 comprising the amino acid sequence of SEQ ID No: 33 and a VL CDR3 comprising the amino acid sequence of SEQ ID No: 34;

Or (iii) a VH CDR1 comprising the amino acid sequence of SEQ ID No: 35 and a VH CDR2 comprising the amino acid sequence of SEQ ID No: 36 and a VH CDR3 comprising the amino acid sequence of SEQ ID No: 37 and a VL CDR1 comprising the amino acid sequence of SEQ ID No: 26 and a VL CDR2 comprising the amino acid sequence of SEQ ID No: 27 and a VL CDR3 comprising the amino acid sequence of SEQ ID No: 28.

2. The method of claim 1, wherein the humanized antibody specifically binds to an epitope within the N-terminal region of human tau.

3. The method of claim 1, wherein the humanized antibody binds the epitope comprising the amino acids at position 3 to 8 located within SEQ ID Nos:1, SEQ ID Nos:2, SEQ ID Nos:3, SEQ ID Nos:4, SEQ ID Nos:5 and SEQ ID Nos:6.

4. The method of claim 1, wherein the humanized antibody comprises:

(i) Heavy chain variable region comprising SEQ ID No:38 and light chain variable region comprising SEQ ID No:39;

Or (ii) Heavy chain variable region comprising SEQ ID No:40 and light chain variable region comprising SEQ ID No:41;

Or (iii) Heavy chain variable region comprising SEQ ID No:42 and light chain variable region comprising SEQ ID No:43;

Or (iv) Heavy chain variable region comprising SEQ ID No:44 and light chain variable region comprising SEQ ID No:45;

Or (v) Heavy chain variable region comprising SEQ ID No:46 and light chain variable region comprising SEQ ID No:47;

Or (vi) Heavy chain variable region comprising SEQ ID No:48 and light chain variable region comprising SEQ ID No:49;

Or (vii) Heavy chain variable region comprising SEQ ID No:50 and light chain variable region comprising SEQ ID No:51.

5. The method of claim 1, wherein the humanized antibody comprises a human light chain framework region and a human heavy chain framework region.

6. The method of claim 1, wherein the humanized antibody comprises a human light chain constant region and human heavy chain constant region.

7. The method of claim 1, wherein the heavy chain constant region of the humanized antibody is selected from the group of human heavy chain constant regions consisting of the isotype IgG1, IgG2, IgG3, and IgG4.

8. The method of claim 1, wherein the humanized antibody comprises antibody Armanezumab comprising the amino acid sequences of SEQ ID No. 54 for VH/CH and SEQ ID No. 55 for VL/CL.

9. The method of claim 1, wherein the humanized antibody is an intact antibody a single-chain Fv fragment, an F(ab') fragment, an F(ab) fragment or an F(ab')2 fragment.

10. The method of claims 1 or 9, wherein the humanized antibody is capable of (i) binding to pathologically aggregated tau and (ii) reducing tau aggregates in the brain and (iii) inhibiting transcellular propagation of pathological, aggregated tau.

11. The method of claims 1 or 9, wherein the pharmaceutical composition administered to an individual in need comprises cells or viruses expressing the humanized antibody.

12. The method of claim 11, wherein the cells is a member selected from the group consisting of T cells, macrophages, dendritic cells and bacteria.

13. The method of claim 11, wherein the virus is a member selected from the group consisting of adenovirus, adeno-associated virus and lentivirus.

* * * * *

```
                            SEQUENCE LISTING

<160> NUMBER OF SEQ ID NOS: 57

<210> SEQ ID NO 1
<211> LENGTH: 352
<212> TYPE: PRT
<213> ORGANISM: Homo sapiens

<400> SEQUENCE: 1

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Ala Glu Glu Ala
        35                  40                  45

Gly Ile Gly Asp Thr Pro Ser Leu Glu Asp Glu Ala Ala Gly His Val
    50                  55                  60

Thr Gln Ala Arg Met Val Ser Lys Ser Lys Asp Gly Thr Gly Ser Asp
65                  70                  75                  80

Asp Lys Lys Ala Lys Gly Ala Asp Gly Lys Thr Lys Ile Ala Thr Pro
                85                  90                  95

Arg Gly Ala Ala Pro Pro Gly Gln Lys Gly Gln Ala Asn Ala Thr Arg
            100                 105                 110

Ile Pro Ala Lys Thr Pro Pro Ala Pro Lys Thr Pro Pro Ser Ser Gly
        115                 120                 125

Glu Pro Pro Lys Ser Gly Asp Arg Ser Gly Tyr Ser Ser Pro Gly Ser
    130                 135                 140

Pro Gly Thr Pro Gly Ser Arg Ser Arg Thr Pro Ser Leu Pro Thr Pro
145                 150                 155                 160

Pro Thr Arg Glu Pro Lys Lys Val Ala Val Arg Thr Pro Pro Lys
                165                 170                 175

Ser Pro Ser Ser Ala Lys Ser Arg Leu Gln Thr Ala Pro Val Pro Met
            180                 185                 190

Pro Asp Leu Lys Asn Val Lys Ser Lys Ile Gly Ser Thr Glu Asn Leu
        195                 200                 205

Lys His Gln Pro Gly Gly Gly Lys Val Gln Ile Val Tyr Lys Pro Val
    210                 215                 220

Asp Leu Ser Lys Val Thr Ser Lys Cys Gly Ser Leu Gly Asn Ile His
225                 230                 235                 240

His Lys Pro Gly Gly Gly Gln Val Glu Val Lys Ser Glu Lys Leu Asp
                245                 250                 255

Phe Lys Asp Arg Val Gln Ser Lys Ile Gly Ser Leu Asp Asn Ile Thr
            260                 265                 270

His Val Pro Gly Gly Gly Asn Lys Lys Ile Glu Thr His Lys Leu Thr
        275                 280                 285

Phe Arg Glu Asn Ala Lys Ala Lys Thr Asp His Gly Ala Glu Ile Val
    290                 295                 300

Tyr Lys Ser Pro Val Val Ser Gly Asp Thr Ser Pro Arg His Leu Ser
305                 310                 315                 320
```

```
Asn Val Ser Ser Thr Gly Ser Ile Asp Met Val Asp Ser Pro Gln Leu
                    325                 330                 335

Ala Thr Leu Ala Asp Glu Val Ser Ala Ser Leu Ala Lys Gln Gly Leu
            340                 345                 350

<210> SEQ ID NO 2
<211> LENGTH: 383
<212> TYPE: PRT
<213> ORGANISM: Homo sapiens

<400> SEQUENCE: 2

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Ala Glu Glu Ala
        35                  40                  45

Gly Ile Gly Asp Thr Pro Ser Leu Glu Asp Glu Ala Ala Gly His Val
    50                  55                  60

Thr Gln Ala Arg Met Val Ser Lys Ser Lys Asp Gly Thr Gly Ser Asp
65                  70                  75                  80

Asp Lys Lys Ala Lys Gly Ala Asp Gly Lys Thr Lys Ile Ala Thr Pro
                85                  90                  95

Arg Gly Ala Ala Pro Pro Gly Gln Lys Gly Gln Ala Asn Ala Thr Arg
            100                 105                 110

Ile Pro Ala Lys Thr Pro Pro Ala Pro Lys Thr Pro Pro Ser Ser Gly
        115                 120                 125

Glu Pro Pro Lys Ser Gly Asp Arg Ser Gly Tyr Ser Ser Pro Gly Ser
    130                 135                 140

Pro Gly Thr Pro Gly Ser Arg Ser Arg Thr Pro Ser Leu Pro Thr Pro
145                 150                 155                 160

Pro Thr Arg Glu Pro Lys Lys Val Ala Val Arg Thr Pro Pro Lys
                165                 170                 175

Ser Pro Ser Ser Ala Lys Ser Arg Leu Gln Thr Ala Pro Val Pro Met
            180                 185                 190

Pro Asp Leu Lys Asn Val Lys Ser Lys Ile Gly Ser Thr Glu Asn Leu
        195                 200                 205

Lys His Gln Pro Gly Gly Gly Lys Val Gln Ile Ile Asn Lys Lys Leu
    210                 215                 220

Asp Leu Ser Asn Val Gln Ser Lys Cys Gly Ser Lys Asp Asn Ile Lys
225                 230                 235                 240

His Val Pro Gly Gly Gly Ser Val Gln Ile Val Tyr Lys Pro Val Asp
                245                 250                 255

Leu Ser Lys Val Thr Ser Lys Cys Gly Ser Leu Gly Asn Ile His His
            260                 265                 270

Lys Pro Gly Gly Gly Gln Val Glu Val Lys Ser Glu Lys Leu Asp Phe
        275                 280                 285

Lys Asp Arg Val Gln Ser Lys Ile Gly Ser Leu Asp Asn Ile Thr His
    290                 295                 300

Val Pro Gly Gly Gly Asn Lys Lys Ile Glu Thr His Lys Leu Thr Phe
305                 310                 315                 320

Arg Glu Asn Ala Lys Ala Lys Thr Asp His Gly Ala Glu Ile Val Tyr
                325                 330                 335

Lys Ser Pro Val Val Ser Gly Asp Thr Ser Pro Arg His Leu Ser Asn
            340                 345                 350
```

```
Val Ser Ser Thr Gly Ser Ile Asp Met Val Asp Ser Pro Gln Leu Ala
    355                 360                 365

Thr Leu Ala Asp Glu Val Ser Ala Ser Leu Ala Lys Gln Gly Leu
    370                 375                 380
```

<210> SEQ ID NO 3
<211> LENGTH: 383
<212> TYPE: PRT
<213> ORGANISM: Homo sapiens

<400> SEQUENCE: 3

```
Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
                20                  25                  30

Gln Asp Gln Glu Gly Asp Thr Asp Ala Gly Leu Lys Ala Glu Glu Ala
            35                  40                  45

Gly Ile Gly Asp Thr Pro Ser Leu Glu Asp Glu Ala Ala Gly His Val
        50                  55                  60

Thr Gln Ala Arg Met Val Ser Lys Ser Lys Asp Gly Thr Gly Ser Asp
65                  70                  75                  80

Asp Lys Lys Ala Lys Gly Ala Asp Gly Lys Thr Lys Ile Ala Thr Pro
                85                  90                  95

Arg Gly Ala Ala Pro Pro Gly Gln Lys Gly Gln Ala Asn Ala Thr Arg
            100                 105                 110

Ile Pro Ala Lys Thr Pro Pro Ala Pro Lys Thr Pro Pro Ser Ser Gly
        115                 120                 125

Glu Pro Pro Lys Ser Gly Asp Arg Ser Gly Tyr Ser Ser Pro Gly Ser
130                 135                 140

Pro Gly Thr Pro Gly Ser Arg Ser Arg Thr Pro Ser Leu Pro Thr Pro
145                 150                 155                 160

Pro Thr Arg Glu Pro Lys Lys Val Ala Val Val Arg Thr Pro Pro Lys
                165                 170                 175

Ser Pro Ser Ser Ala Lys Ser Arg Leu Gln Thr Ala Pro Val Pro Met
            180                 185                 190

Pro Asp Leu Lys Asn Val Lys Ser Lys Ile Gly Ser Thr Glu Asn Leu
        195                 200                 205

Lys His Gln Pro Gly Gly Gly Lys Val Gln Ile Ile Asn Lys Lys Leu
    210                 215                 220

Asp Leu Ser Asn Val Gln Ser Lys Cys Gly Ser Lys Asp Asn Ile Lys
225                 230                 235                 240

His Val Pro Gly Gly Gly Ser Val Gln Ile Val Tyr Lys Pro Val Asp
                245                 250                 255

Leu Ser Lys Val Thr Ser Lys Cys Gly Ser Leu Gly Asn Ile His His
            260                 265                 270

Lys Pro Gly Gly Gly Gln Val Glu Val Lys Ser Glu Lys Leu Asp Phe
        275                 280                 285

Lys Asp Arg Val Gln Ser Lys Ile Gly Ser Leu Asp Asn Ile Thr His
    290                 295                 300

Val Pro Gly Gly Gly Asn Lys Lys Ile Glu Thr His Lys Leu Thr Phe
305                 310                 315                 320

Arg Glu Asn Ala Lys Ala Lys Thr Asp His Gly Ala Glu Ile Val Tyr
                325                 330                 335

Lys Ser Pro Val Val Ser Gly Asp Thr Ser Pro Arg His Leu Ser Asn
            340                 345                 350
```

```
Val Ser Ser Thr Gly Ser Ile Asp Met Val Asp Ser Pro Gln Leu Ala
        355                 360                 365

Thr Leu Ala Asp Glu Val Ser Ala Ser Leu Ala Lys Gln Gly Leu
    370                 375                 380

<210> SEQ ID NO 4
<211> LENGTH: 412
<212> TYPE: PRT
<213> ORGANISM: Homo sapiens

<400> SEQUENCE: 4

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Pro Gly Ser Glu Thr Ser
    50                  55                  60

Asp Ala Lys Ser Thr Pro Thr Ala Glu Ala Glu Glu Ala Gly Ile Gly
65                  70                  75                  80

Asp Thr Pro Ser Leu Glu Asp Glu Ala Ala Gly His Val Thr Gln Ala
                85                  90                  95

Arg Met Val Ser Lys Ser Lys Asp Gly Thr Gly Ser Asp Asp Lys Lys
            100                 105                 110

Ala Lys Gly Ala Asp Gly Lys Thr Lys Ile Ala Thr Pro Arg Gly Ala
        115                 120                 125

Ala Pro Pro Gly Gln Lys Gly Gln Ala Asn Ala Thr Arg Ile Pro Ala
    130                 135                 140

Lys Thr Pro Pro Ala Pro Lys Thr Pro Ser Ser Gly Glu Pro Pro
145                 150                 155                 160

Lys Ser Gly Asp Arg Ser Gly Tyr Ser Ser Pro Gly Ser Pro Gly Thr
                165                 170                 175

Pro Gly Ser Arg Ser Arg Thr Pro Ser Leu Pro Thr Pro Pro Thr Arg
            180                 185                 190

Glu Pro Lys Lys Val Ala Val Val Arg Thr Pro Pro Lys Ser Pro Ser
        195                 200                 205

Ser Ala Lys Ser Arg Leu Gln Thr Ala Pro Val Pro Met Pro Asp Leu
    210                 215                 220

Lys Asn Val Lys Ser Lys Ile Gly Ser Thr Glu Asn Leu Lys His Gln
225                 230                 235                 240

Pro Gly Gly Gly Lys Val Gln Ile Ile Asn Lys Lys Leu Asp Leu Ser
                245                 250                 255

Asn Val Gln Ser Lys Cys Gly Ser Lys Asp Asn Ile Lys His Val Pro
            260                 265                 270

Gly Gly Gly Ser Val Gln Ile Val Tyr Lys Pro Val Asp Leu Ser Lys
        275                 280                 285

Val Thr Ser Lys Cys Gly Ser Leu Gly Asn Ile His His Lys Pro Gly
    290                 295                 300

Gly Gly Gln Val Glu Val Lys Ser Glu Lys Leu Asp Phe Lys Asp Arg
305                 310                 315                 320

Val Gln Ser Lys Ile Gly Ser Leu Asp Asn Ile Thr His Val Pro Gly
                325                 330                 335

Gly Gly Asn Lys Lys Ile Glu Thr His Lys Leu Thr Phe Arg Glu Asn
            340                 345                 350
```

```
Ala Lys Ala Lys Thr Asp His Gly Ala Glu Ile Val Tyr Lys Ser Pro
            355                 360                 365

Val Val Ser Gly Asp Thr Ser Pro Arg His Leu Ser Asn Val Ser Ser
370                 375                 380

Thr Gly Ser Ile Asp Met Val Asp Ser Pro Gln Leu Ala Thr Leu Ala
385                 390                 395                 400

Asp Glu Val Ser Ala Ser Leu Ala Lys Gln Gly Leu
                405                 410

<210> SEQ ID NO 5
<211> LENGTH: 410
<212> TYPE: PRT
<213> ORGANISM: Homo sapiens

<400> SEQUENCE: 5

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Ala Gln Pro His Thr Glu
                85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Ala Arg Met Val
        115                 120                 125

Ser Lys Ser Lys Asp Gly Thr Gly Ser Asp Asp Lys Lys Ala Lys Gly
    130                 135                 140

Ala Asp Gly Lys Thr Lys Ile Ala Thr Pro Arg Gly Ala Ala Pro Pro
145                 150                 155                 160

Gly Gln Lys Gly Gln Ala Asn Ala Thr Arg Ile Pro Ala Lys Thr Pro
                165                 170                 175

Pro Ala Pro Lys Thr Pro Pro Ser Ser Gly Glu Pro Pro Lys Ser Gly
            180                 185                 190

Asp Arg Ser Gly Tyr Ser Ser Pro Gly Ser Pro Gly Thr Pro Gly Ser
        195                 200                 205

Arg Ser Arg Thr Pro Ser Leu Pro Thr Pro Pro Thr Arg Glu Pro Lys
    210                 215                 220

Lys Val Ala Val Val Arg Thr Pro Pro Lys Ser Pro Ser Ser Ala Lys
225                 230                 235                 240

Ser Arg Leu Gln Thr Ala Pro Val Pro Met Pro Asp Leu Lys Asn Val
                245                 250                 255

Lys Ser Lys Ile Gly Ser Thr Glu Asn Leu Lys His Gln Pro Gly Gly
            260                 265                 270

Gly Lys Val Gln Ile Val Tyr Lys Pro Val Asp Leu Ser Lys Val Thr
        275                 280                 285

Ser Lys Cys Gly Ser Leu Gly Asn Ile His His Lys Pro Gly Gly Gly
    290                 295                 300

Gln Val Glu Val Lys Ser Glu Lys Leu Asp Phe Lys Asp Arg Val Gln
305                 310                 315                 320
```

```
Ser Lys Ile Gly Ser Leu Asp Asn Ile Thr His Val Pro Gly Gly Gly
            325                 330                 335

Asn Lys Lys Ile Glu Thr His Lys Leu Thr Phe Arg Glu Asn Ala Lys
            340                 345                 350

Ala Lys Thr Asp His Gly Ala Glu Ile Val Tyr Lys Ser Pro Val Val
            355                 360                 365

Ser Gly Asp Thr Ser Pro Arg His Leu Ser Asn Val Ser Ser Thr Gly
            370                 375                 380

Ser Ile Asp Met Val Asp Ser Pro Gln Leu Ala Thr Leu Ala Asp Glu
385                 390                 395                 400

Val Ser Ala Ser Leu Ala Lys Gln Gly Leu
            405                 410

<210> SEQ ID NO 6
<211> LENGTH: 441
<212> TYPE: PRT
<213> ORGANISM: Homo sapiens

<400> SEQUENCE: 6

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Ala Gln Pro His Thr Glu
                85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Ala Arg Met Val
        115                 120                 125

Ser Lys Ser Lys Asp Gly Thr Gly Ser Asp Asp Lys Lys Ala Lys Gly
    130                 135                 140

Ala Asp Gly Lys Thr Lys Ile Ala Thr Pro Arg Gly Ala Ala Pro Pro
145                 150                 155                 160

Gly Gln Lys Gly Gln Ala Asn Ala Thr Arg Ile Pro Ala Lys Thr Pro
                165                 170                 175

Pro Ala Pro Lys Thr Pro Pro Ser Ser Gly Glu Pro Pro Lys Ser Gly
            180                 185                 190

Asp Arg Ser Gly Tyr Ser Ser Pro Gly Ser Pro Gly Thr Pro Gly Ser
        195                 200                 205

Arg Ser Arg Thr Pro Ser Leu Pro Thr Pro Pro Thr Arg Glu Pro Lys
    210                 215                 220

Lys Val Ala Val Val Arg Thr Pro Pro Lys Ser Pro Ser Ser Ala Lys
225                 230                 235                 240

Ser Arg Leu Gln Thr Ala Pro Val Pro Met Pro Asp Leu Lys Asn Val
                245                 250                 255

Lys Ser Lys Ile Gly Ser Thr Glu Asn Leu Lys His Gln Pro Gly Gly
            260                 265                 270

Gly Lys Val Gln Ile Ile Asn Lys Lys Leu Asp Leu Ser Asn Val Gln
        275                 280                 285
```

```
Ser Lys Cys Gly Ser Lys Asp Asn Ile Lys His Val Pro Gly Gly Gly
    290                 295                 300
Ser Val Gln Ile Val Tyr Lys Pro Val Asp Leu Ser Lys Val Thr Ser
305                 310                 315                 320
Lys Cys Gly Ser Leu Gly Asn Ile His His Lys Pro Gly Gly Gly Gln
                325                 330                 335
Val Glu Val Lys Ser Glu Lys Leu Asp Phe Lys Asp Arg Val Gln Ser
                340                 345                 350
Lys Ile Gly Ser Leu Asp Asn Ile Thr His Val Pro Gly Gly Gly Asn
            355                 360                 365
Lys Lys Ile Glu Thr His Lys Leu Thr Phe Arg Glu Asn Ala Lys Ala
    370                 375                 380
Lys Thr Asp His Gly Ala Glu Ile Val Tyr Lys Ser Pro Val Val Ser
385                 390                 395                 400
Gly Asp Thr Ser Pro Arg His Leu Ser Asn Val Ser Ser Thr Gly Ser
                405                 410                 415
Ile Asp Met Val Asp Ser Pro Gln Leu Ala Thr Leu Ala Asp Glu Val
                420                 425                 430
Ser Ala Ser Leu Ala Lys Gln Gly Leu
            435                 440

<210> SEQ ID NO 7
<211> LENGTH: 17
<212> TYPE: PRT
<213> ORGANISM: Homo sapiens

<400> SEQUENCE: 7

Ala Glu Pro Arg Gln Glu Phe Glu Val Met Glu Asp His Ala Gly Thr
1               5                   10                  15

Tyr

<210> SEQ ID NO 8
<211> LENGTH: 35
<212> TYPE: PRT
<213> ORGANISM: Homo sapiens

<400> SEQUENCE: 8

Ala Glu Pro Arg Gln Glu Phe Glu Val Met Glu Asp His Ala Gly Thr
1               5                   10                  15

Tyr Gly Leu Gly Asp Arg Lys Asp Gln Gly Gly Tyr Thr Met His Gln
            20                  25                  30

Asp Gln Glu
        35

<210> SEQ ID NO 9
<211> LENGTH: 11
<212> TYPE: PRT
<213> ORGANISM: Human immunodeficiency virus

<400> SEQUENCE: 9

Tyr Gly Arg Lys Lys Arg Arg Gln Arg Arg Arg
1               5                   10

<210> SEQ ID NO 10
<211> LENGTH: 10
<212> TYPE: PRT
<213> ORGANISM: Homo sapiens
```

```
<400> SEQUENCE: 10

Met Ile Ile Tyr Arg Asp Leu Ile Ser His
1               5                   10

<210> SEQ ID NO 11
<211> LENGTH: 14
<212> TYPE: PRT
<213> ORGANISM: Drosophila melanogaster

<400> SEQUENCE: 11

Arg Gln Ile Lys Ile Trp Phe Gln Asn Arg Arg Met Lys Trp
1               5                   10

<210> SEQ ID NO 12
<211> LENGTH: 18
<212> TYPE: PRT
<213> ORGANISM: Artificial sequence
<220> FEATURE:
<223> OTHER INFORMATION: Synthetic

<400> SEQUENCE: 12

Lys Leu Ala Leu Lys Leu Ala Leu Lys Ala Leu Lys Ala Ala Leu Lys
1               5                   10                  15

Leu Ala

<210> SEQ ID NO 13
<211> LENGTH: 27
<212> TYPE: PRT
<213> ORGANISM: Homo sapiens

<400> SEQUENCE: 13

Gly Trp Thr Leu Asn Ser Ala Gly Tyr Leu Leu Gly Lys Ile Asn Leu
1               5                   10                  15

Lys Ala Leu Ala Ala Leu Ala Lys Lys Ile Leu
            20                  25

<210> SEQ ID NO 14
<211> LENGTH: 27
<212> TYPE: PRT
<213> ORGANISM: Simian virus 40

<400> SEQUENCE: 14

Gly Ala Leu Phe Leu Gly Trp Leu Gly Ala Ala Gly Ser Thr Met Gly
1               5                   10                  15

Ala Trp Ser Gln Pro Lys Lys Lys Arg Lys Val
            20                  25

<210> SEQ ID NO 15
<211> LENGTH: 18
<212> TYPE: PRT
<213> ORGANISM: Homo sapiens

<400> SEQUENCE: 15

Arg Gly Gly Arg Leu Ser Tyr Ser Arg Arg Arg Phe Ser Thr Ser Thr
1               5                   10                  15

Gly Arg

<210> SEQ ID NO 16
<211> LENGTH: 10
<212> TYPE: PRT
<213> ORGANISM: Homo sapiens
```

<400> SEQUENCE: 16

Arg Arg Leu Ser Tyr Ser Arg Arg Arg Phe
1               5                   10

<210> SEQ ID NO 17
<211> LENGTH: 140
<212> TYPE: PRT
<213> ORGANISM: Mus musculus

<400> SEQUENCE: 17

Met Glu Cys Asn Trp Ile Leu Pro Phe Ile Leu Ser Val Thr Ser Gly
1               5                   10                  15

Val Tyr Ser Glu Val Gln Leu Gln Gln Ser Gly Thr Val Leu Ala Arg
            20                  25                  30

Pro Gly Ala Ser Val Lys Met Ser Cys Lys Thr Ser Gly Tyr Thr Phe
        35                  40                  45

Thr Asn His Trp Met His Trp Val Lys Gln Arg Pro Gly Gln Gly Leu
    50                  55                  60

Glu Trp Ile Gly Ala Ile Asp Pro Gly Asn Ser Asp Thr Ser Tyr Asn
65                  70                  75                  80

Gln Lys Phe Lys Gly Gln Ala Lys Leu Thr Ala Val Thr Ser Ala Ser
                85                  90                  95

Thr Ala Phe Met Glu Leu Ser Ser Leu Thr Asn Glu Asp Ser Ala Val
            100                 105                 110

Tyr Tyr Cys Thr Arg Arg Asp Phe Phe Gly Gly Glu Tyr Ala Val Asp
        115                 120                 125

Tyr Trp Gly Gln Gly Thr Ser Val Thr Val Ser Ser
    130                 135                 140

<210> SEQ ID NO 18
<211> LENGTH: 131
<212> TYPE: PRT
<213> ORGANISM: Mus musculus

<400> SEQUENCE: 18

Met Lys Leu Pro Val Arg Leu Leu Val Leu Met Phe Trp Ile Pro Ala
1               5                   10                  15

Ser Ser Ser Asp Val Val Met Thr Gln Thr Pro Leu Ser Leu Pro Val
            20                  25                  30

Ser Leu Gly Asp Gln Ala Ser Ile Ser Cys Arg Ser Ser Gln Ser Leu
        35                  40                  45

Val His Ser Asn Gly Asn Thr Tyr Leu His Trp Tyr Leu Gln Lys Pro
    50                  55                  60

Gly Gln Ser Pro Lys Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Val Tyr Phe Cys
            100                 105                 110

Ser Gln Ser Thr His Val Pro Trp Thr Phe Gly Gly Gly Thr Lys Leu
        115                 120                 125

Glu Ile Lys
    130

<210> SEQ ID NO 19
<211> LENGTH: 133
<212> TYPE: PRT
<213> ORGANISM: Mus musculus

<400> SEQUENCE: 19

Met Lys Val Leu Ser Leu Leu Tyr Leu Leu Thr Ala Ile Pro Gly Ile
1               5                   10                  15

Leu Ser Asp Val Gln Leu Gln Glu Ser Gly Pro Gly Leu Val Lys Pro
            20                  25                  30

Ser Gln Ser Leu Ser Leu Thr Cys Ser Val Thr Gly Tyr Ser Ile Thr
        35                  40                  45

Ser Gly Tyr Tyr Tyr Asn Trp Ile Arg Gln Phe Pro Gly Asn Lys Leu
    50                  55                  60

Glu Trp Met Gly Tyr Ile Arg Asn Asp Gly Ser Asn Asn Tyr Asn Pro
65                  70                  75                  80

Ser Leu Lys Asn Arg Ile Ser Ile Thr Arg Asp Thr Ser Lys Asn Gln
                85                  90                  95

Phe Phe Leu Lys Leu Asn Ser Val Thr Thr Glu Asp Ser Ala Thr Tyr
            100                 105                 110

Tyr Cys Ala Arg Gly Leu Thr Pro Asp Tyr Trp Gly Gln Gly Ile Thr
        115                 120                 125

Leu Thr Val Ser Ser
    130

<210> SEQ ID NO 20
<211> LENGTH: 131
<212> TYPE: PRT
<213> ORGANISM: Mus musculus

<400> SEQUENCE: 20

Met Lys Leu Pro Val Arg Leu Leu Val Leu Met Phe Trp Ile Pro Ala
1               5                   10                  15

Ser Ser Ser Asp Val Val Met Thr Gln Thr Pro Leu Ser Leu Pro Val
            20                  25                  30

Ser Leu Gly Asp Gln Ala Ser Ile Ser Cys Arg Ser Ser Gln Ser Leu
        35                  40                  45

Leu His Ser Asn Gly Asn Thr Tyr Leu His Trp Tyr Leu Gln Lys Pro
    50                  55                  60

Gly Gln Ser Pro Lys Leu Leu Ile Tyr Lys Val Ser Asp Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Leu Glu Ala Glu Asp Leu Gly Val Phe Phe Cys
            100                 105                 110

Ser Gln Thr Thr His Val Pro Leu Thr Phe Gly Ala Gly Thr Lys Leu
        115                 120                 125

Glu Leu Lys
    130

<210> SEQ ID NO 21
<211> LENGTH: 140
<212> TYPE: PRT
<213> ORGANISM: Mus musculus

```
<400> SEQUENCE: 21

Met Glu Cys Asn Trp Ile Leu Pro Phe Ile Leu Ser Val Thr Ser Gly
1               5                   10                  15

Val Tyr Ser Glu Val Gln Leu Gln Gln Ser Gly Thr Val Leu Ala Arg
            20                  25                  30

Pro Gly Ala Ser Val Lys Met Ser Cys Lys Thr Ser Gly Tyr Thr Phe
        35                  40                  45

Thr Thr Tyr Trp Ile His Trp Val Lys Gln Arg Pro Gly Gln Gly Leu
    50                  55                  60

Glu Trp Ile Gly Ala Ile Cys Pro Gly Asp Ser Asp Thr Ser Tyr Asn
65                  70                  75                  80

Gln Lys Phe Lys Gly Gln Ala Lys Leu Thr Ala Val Pro Ser Ala Ser
                85                  90                  95

Thr Ala Tyr Met Glu Leu Ser Ser Leu Thr Ile Glu Asp Ser Ala Val
            100                 105                 110

Tyr Tyr Cys Thr Arg Arg Asp Phe Tyr Gly Ser Asp Tyr Ala Val Asp
        115                 120                 125

Tyr Trp Gly Gln Gly Thr Ser Val Thr Val Ser Ser
    130                 135                 140

<210> SEQ ID NO 22
<211> LENGTH: 131
<212> TYPE: PRT
<213> ORGANISM: Mus musculus

<400> SEQUENCE: 22

Met Lys Leu Pro Val Arg Leu Leu Val Leu Met Phe Trp Ile Pro Ala
1               5                   10                  15

Ser Ser Ser Asp Val Val Met Thr Gln Thr Pro Leu Ser Leu Pro Val
            20                  25                  30

Ser Leu Gly Asp Gln Ala Ser Ile Ser Cys Arg Ser Ser Gln Ser Leu
        35                  40                  45

Val His Ser Asn Gly Asn Thr Tyr Leu His Trp Tyr Leu Gln Lys Pro
    50                  55                  60

Gly Gln Ser Pro Lys Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Gly Glu Asp Leu Gly Val Tyr Phe Cys
            100                 105                 110

Ser Gln Ser Thr His Val Pro Trp Thr Phe Gly Gly Gly Thr Lys Leu
        115                 120                 125

Glu Ile Lys
    130

<210> SEQ ID NO 23
<211> LENGTH: 5
<212> TYPE: PRT
<213> ORGANISM: Mus musculus

<400> SEQUENCE: 23

Asn His Trp Met His
1               5
```

<210> SEQ ID NO 24
<211> LENGTH: 17
<212> TYPE: PRT
<213> ORGANISM: Mus musculus

<400> SEQUENCE: 24

```
Ala Ile Asp Pro Gly Asn Ser Asp Thr Ser Tyr Asn Gln Lys Phe Lys
1               5                   10                  15
Gly
```

<210> SEQ ID NO 25
<211> LENGTH: 12
<212> TYPE: PRT
<213> ORGANISM: Mus musculus

<400> SEQUENCE: 25

```
Arg Asp Phe Phe Gly Gly Glu Tyr Ala Val Asp Tyr
1               5                   10
```

<210> SEQ ID NO 26
<211> LENGTH: 16
<212> TYPE: PRT
<213> ORGANISM: Mus musculus

<400> SEQUENCE: 26

```
Arg Ser Ser Gln Ser Leu Val His Ser Asn Gly Asn Thr Tyr Leu His
1               5                   10                  15
```

<210> SEQ ID NO 27
<211> LENGTH: 7
<212> TYPE: PRT
<213> ORGANISM: Mus musculus

<400> SEQUENCE: 27

```
Lys Val Ser Asn Arg Phe Ser
1               5
```

<210> SEQ ID NO 28
<211> LENGTH: 9
<212> TYPE: PRT
<213> ORGANISM: Mus musculus

<400> SEQUENCE: 28

```
Ser Gln Ser Thr His Val Pro Trp Thr
1               5
```

<210> SEQ ID NO 29
<211> LENGTH: 6
<212> TYPE: PRT
<213> ORGANISM: mus musculus

<400> SEQUENCE: 29

```
Ser Gly Tyr Tyr Tyr Asn
1               5
```

<210> SEQ ID NO 30
<211> LENGTH: 16
<212> TYPE: PRT
<213> ORGANISM: mus musculus

<400> SEQUENCE: 30

```
Tyr Ile Arg Asn Asp Gly Ser Asn Asn Tyr Asn Pro Ser Leu Lys Asn
1               5                   10                  15
```

```
<210> SEQ ID NO 31
<211> LENGTH: 6
<212> TYPE: PRT
<213> ORGANISM: mus musculus

<400> SEQUENCE: 31

Gly Leu Thr Pro Asp Tyr
1               5

<210> SEQ ID NO 32
<211> LENGTH: 16
<212> TYPE: PRT
<213> ORGANISM: mus musculus

<400> SEQUENCE: 32

Arg Ser Ser Gln Ser Leu Leu His Ser Asn Gly Asn Thr Tyr Leu His
1               5                   10                  15

<210> SEQ ID NO 33
<211> LENGTH: 7
<212> TYPE: PRT
<213> ORGANISM: mus musculus

<400> SEQUENCE: 33

Lys Val Ser Asp Arg Phe Ser
1               5

<210> SEQ ID NO 34
<211> LENGTH: 9
<212> TYPE: PRT
<213> ORGANISM: mus musculus

<400> SEQUENCE: 34

Ser Gln Thr Thr His Val Pro Leu Thr
1               5

<210> SEQ ID NO 35
<211> LENGTH: 5
<212> TYPE: PRT
<213> ORGANISM: mus musculus

<400> SEQUENCE: 35

Thr Tyr Trp Ile His
1               5

<210> SEQ ID NO 36
<211> LENGTH: 17
<212> TYPE: PRT
<213> ORGANISM: mus musculus

<400> SEQUENCE: 36

Ala Ile Cys Pro Gly Asp Ser Asp Thr Ser Tyr Asn Gln Lys Phe Lys
1               5                   10                  15

Gly

<210> SEQ ID NO 37
<211> LENGTH: 12
<212> TYPE: PRT
<213> ORGANISM: mus musculus

<400> SEQUENCE: 37

Arg Asp Phe Tyr Gly Ser Asp Tyr Ala Val Asp Tyr
1               5                   10
```

```
<210> SEQ ID NO 38
<211> LENGTH: 121
<212> TYPE: PRT
<213> ORGANISM: Artificial sequence
<220> FEATURE:
<223> OTHER INFORMATION: humanized mouse Ig

<400> SEQUENCE: 38

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn His
            20                  25                  30

Trp Met His Trp Val Arg Gln Ala Pro Gly Gln Gly Leu Glu Trp Met
        35                  40                  45

Gly Ala Ile Asp Pro Gly Asn Ser Asp Thr Ser Tyr Asn Gln Lys Phe
    50                  55                  60

Lys Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Arg Asp Phe Phe Gly Gly Glu Tyr Ala Val Asp Tyr Trp Gly
            100                 105                 110

Gln Gly Thr Thr Val Thr Val Ser Ser
        115                 120

<210> SEQ ID NO 39
<211> LENGTH: 112
<212> TYPE: PRT
<213> ORGANISM: Artificial sequence
<220> FEATURE:
<223> OTHER INFORMATION: Humanized mouse Ig

<400> SEQUENCE: 39

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Leu Val His Ser
            20                  25                  30

Asn Gly Asn Thr Tyr Leu His Trp Tyr Gln Gln Lys Pro Gly Gln Ala
        35                  40                  45

Pro Arg Leu Leu Ile Tyr Lys Val Ser Asn Arg Phe Ser Gly Ile Pro
    50                  55                  60

Asp Arg Phe Ser Gly Ser Gly Ser Gly Thr Asp Phe Thr Leu Thr Ile
65                  70                  75                  80

Ser Arg Leu Glu Pro Glu Asp Phe Ala Val Tyr Tyr Cys Ser Gln Ser
                85                  90                  95

Thr His Val Pro Trp Thr Phe Gly Gly Gly Thr Lys Val Glu Ile Lys
            100                 105                 110

<210> SEQ ID NO 40
<211> LENGTH: 121
<212> TYPE: PRT
<213> ORGANISM: Artificial sequence
<220> FEATURE:
<223> OTHER INFORMATION: humanized mouse Ig

<400> SEQUENCE: 40

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Thr Phe Thr Asn His
            20                  25                  30
```

-continued

```
Trp Met His Trp Val Gln Gln Ala Pro Gly Lys Gly Leu Glu Trp Met
         35                  40                  45

Gly Ala Ile Asp Pro Gly Asn Ser Asp Thr Ser Tyr Asn Gln Lys Phe
 50                  55                  60

Lys Gly Arg Val Thr Ile Thr Arg Asp Thr Ser Ala Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Arg Asp Phe Phe Gly Gly Glu Tyr Ala Val Asp Tyr Trp Gly
            100                 105                 110

Gln Gly Thr Thr Val Thr Val Ser Ser
            115                 120
```

<210> SEQ ID NO 41
<211> LENGTH: 112
<212> TYPE: PRT
<213> ORGANISM: Artificial sequence
<220> FEATURE:
<223> OTHER INFORMATION: Humanized mouse Ig

<400> SEQUENCE: 41

```
Asp Ile Val Met Thr Gln Thr Pro Leu Ser Leu Ser Val Thr Pro Gly
 1               5                  10                  15

Gln Pro Ala Ser Ile Ser Cys Arg Ser Ser Gln Ser Leu Val His Ser
             20                  25                  30

Asn Gly Asn Thr Tyr Leu His Trp Tyr Gln Gln Lys Pro Gly Gln Ala
         35                  40                  45

Pro Arg Leu Leu Ile Tyr Lys Val Ser Asn Arg Phe Ser Gly Val Pro
 50                  55                  60

Asp Arg Phe Ser Gly Ser Gly Ala Gly Thr Asp Phe Thr Leu Lys Ile
 65                  70                  75                  80

Ser Arg Val Glu Ala Glu Asp Val Gly Val Tyr Tyr Cys Ser Gln Ser
                 85                  90                  95

Thr His Val Pro Trp Thr Phe Gly Gly Gly Thr Lys Val Glu Ile Lys
            100                 105                 110
```

<210> SEQ ID NO 42
<211> LENGTH: 121
<212> TYPE: PRT
<213> ORGANISM: Artificial sequence
<220> FEATURE:
<223> OTHER INFORMATION: Humanized mouse Ig

<400> SEQUENCE: 42

```
Gln Val Gln Leu Val Gln Ser Gly Ser Glu Leu Lys Lys Pro Gly Ala
 1               5                  10                  15

Ser Val Lys Val Ser Cys Lys Ala Ser Gly Tyr Thr Phe Thr Asn His
             20                  25                  30

Trp Met His Trp Val Arg Gln Ala Pro Gly Lys Gly Leu Glu Trp Val
         35                  40                  45

Gly Ala Ile Asp Pro Gly Asn Ser Asp Thr Ser Tyr Asn Gln Lys Phe
 50                  55                  60

Lys Gly Arg Val Thr Met Thr Arg Asn Thr Ser Ile Ser Thr Ala Tyr
 65                  70                  75                  80

Met Glu Leu Ser Ser Leu Arg Ser Glu Asp Thr Ala Val Tyr Tyr Cys
                 85                  90                  95
```

Ala Arg Arg Asp Phe Phe Gly Gly Glu Tyr Ala Val Asp Tyr Trp Gly
            100                 105                 110

Gln Gly Thr Thr Val Thr Val Ser Ser
        115                 120

<210> SEQ ID NO 43
<211> LENGTH: 112
<212> TYPE: PRT
<213> ORGANISM: Artificial sequence
<220> FEATURE:
<223> OTHER INFORMATION: Humanized mouse Ig

<400> SEQUENCE: 43

Glu Ile Val Met Thr Gln Ser Pro Ala Thr Leu Ser Val Ser Pro Gly
1               5                   10                  15

Glu Arg Ala Thr Leu Ser Cys Arg Ser Ser Gln Ser Leu Val His Ser
            20                  25                  30

Asn Gly Asn Thr Tyr Leu His Trp Tyr Gln Gln Lys Pro Gly Gln Ala
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Trp Thr Phe Gly Gly Gly Thr Lys Val Glu Ile Lys
            100                 105                 110

<210> SEQ ID NO 44
<211> LENGTH: 121
<212> TYPE: PRT
<213> ORGANISM: Artificial seqience
<220> FEATURE:
<223> OTHER INFORMATION: Humanized mouse Ig

<400> SEQUENCE: 44

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn His
            20                  25                  30

Trp Met His Trp Val Gln Gln Ser Pro Gly Gln Gly Leu Glu Trp Met
        35                  40                  45

Gly Ala Ile Asp Pro Gly Asn Ser Asp Thr Ser Tyr Asn Gln Lys Phe
    50                  55                  60

Lys Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Arg Asp Phe Phe Gly Gly Glu Tyr Ala Val Asp Tyr Trp Gly
            100                 105                 110

Gln Gly Thr Thr Val Thr Val Ser Ser
        115                 120

<210> SEQ ID NO 45
<211> LENGTH: 112
<212> TYPE: PRT
<213> ORGANISM: Artificial sequence
<220> FEATURE:
<223> OTHER INFORMATION: Humanized mouse Ig

```
<400> SEQUENCE: 45

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Leu Val His Ser
            20                  25                  30

Asn Gly Asn Thr Tyr Leu His Trp Tyr Gln Gln Lys Pro Gly Lys Ala
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65              70                  75                  80

Ser Arg Val Glu Ala Glu Asp Val Gly Val Tyr Tyr Cys Ser Gln Ser
            85                  90                  95

Thr His Val Pro Trp Thr Phe Gly Gly Gly Thr Lys Val Glu Ile Lys
            100                 105                 110

<210> SEQ ID NO 46
<211> LENGTH: 121
<212> TYPE: PRT
<213> ORGANISM: Artificial sequence
<220> FEATURE:
<223> OTHER INFORMATION: Humanized mouse Ig

<400> SEQUENCE: 46

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn His
            20                  25                  30

Trp Met His Trp Val Arg Gln Ala Pro Gly Lys Gly Leu Glu Trp Val
        35                  40                  45

Gly Ala Ile Asp Pro Gly Asn Ser Asp Thr Ser Tyr Asn Gln Lys Phe
    50                  55                  60

Lys Gly Arg Val Thr Ile Thr Ala Asp Lys Ser Thr Ser Thr Ala Tyr
65              70                  75                  80

Met Glu Leu Ser Ser Leu Arg Ser Glu Asp Thr Ala Val Tyr Tyr Cys
            85                  90                  95

Ala Arg Arg Asp Phe Phe Gly Gly Glu Tyr Ala Val Asp Tyr Trp Gly
            100                 105                 110

Gln Gly Thr Thr Val Thr Val Ser Ser
        115                 120

<210> SEQ ID NO 47
<211> LENGTH: 112
<212> TYPE: PRT
<213> ORGANISM: Artificial sequence
<220> FEATURE:
<223> OTHER INFORMATION: Humanized mouse Ig

<400> SEQUENCE: 47

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Leu Val His Ser
            20                  25                  30

Asn Gly Asn Thr Tyr Leu His Trp Tyr Gln Gln Lys Pro Gly Lys Ala
        35                  40                  45

Pro Lys Leu Leu Ile Tyr Lys Val Ser Asn Arg Phe Ser Gly Ile Pro
    50                  55                  60
```

```
Asp Arg Phe Ser Gly Ser Gly Ser Gly Thr Asp Phe Thr Leu Thr Ile
 65                  70                  75                  80

Ser Arg Leu Glu Pro Glu Asp Phe Ala Val Tyr Tyr Cys Ser Gln Ser
                 85                  90                  95

Thr His Val Pro Trp Thr Phe Gly Gly Gly Thr Lys Val Glu Ile Lys
            100                 105                 110

<210> SEQ ID NO 48
<211> LENGTH: 121
<212> TYPE: PRT
<213> ORGANISM: Artificial sequence
<220> FEATURE:
<223> OTHER INFORMATION: Humanized mouse Ig

<400> SEQUENCE: 48

Gln Val Gln Leu Val Gln Ser Gly Ser Glu Leu Lys Lys Pro Gly Ala
 1               5                  10                  15

Ser Val Lys Val Ser Cys Lys Ala Ser Gly Tyr Thr Phe Thr Asn His
                 20                  25                  30

Trp Met His Trp Val Arg Gln Ala Pro Gly Gln Gly Leu Glu Trp Met
             35                  40                  45

Gly Ala Ile Asp Pro Gly Asn Ser Asp Thr Ser Tyr Asn Gln Lys Phe
 50                  55                  60

Lys Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg Arg Asp Phe Phe Gly Gly Glu Tyr Ala Val Asp Tyr Trp Gly
            100                 105                 110

Gln Gly Thr Thr Val Thr Val Ser Ser
            115                 120

<210> SEQ ID NO 49
<211> LENGTH: 112
<212> TYPE: PRT
<213> ORGANISM: Artificial sequence
<220> FEATURE:
<223> OTHER INFORMATION: Humanized mouse Ig

<400> SEQUENCE: 49

Asp Ile Val Met Thr Gln Thr Pro Leu Ser Leu Ser Val Thr Pro Gly
 1               5                  10                  15

Gln Pro Ala Ser Ile Ser Cys Arg Ser Ser Gln Ser Leu Val His Ser
                 20                  25                  30

Asn Gly Asn Thr Tyr Leu His Trp Tyr Gln Gln Lys Pro Gly Gln Ala
             35                  40                  45

Pro Arg Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Phe Gly Val Tyr Tyr Cys Ser Gln Ser
                 85                  90                  95

Thr His Val Pro Trp Thr Phe Gly Gly Gly Thr Lys Val Glu Ile Lys
            100                 105                 110

<210> SEQ ID NO 50
<211> LENGTH: 121
<212> TYPE: PRT
<213> ORGANISM: Artificial sequence
```

```
<220> FEATURE:
<223> OTHER INFORMATION: Humanized mouse Ig

<400> SEQUENCE: 50

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn His
            20                  25                  30

Trp Met His Trp Val Arg Gln Ala Pro Gly Gln Arg Leu Glu Trp Met
        35                  40                  45

Gly Ala Ile Asp Pro Gly Asn Ser Asp Thr Ser Tyr Asn Gln Lys Phe
    50                  55                  60

Lys Gly Gln Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala Arg Arg Asp Phe Phe Gly Gly Glu Tyr Ala Val Asp Tyr Trp Gly
            100                 105                 110

Gln Gly Thr Thr Val Thr Val Ser Ser
        115                 120

<210> SEQ ID NO 51
<211> LENGTH: 112
<212> TYPE: PRT
<213> ORGANISM: Artificial sequence
<220> FEATURE:
<223> OTHER INFORMATION: Humanized mouse Ig

<400> SEQUENCE: 51

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Leu Val His Ser
            20                  25                  30

Asn Gly Asn Thr Tyr Leu His Trp Tyr Gln Gln Lys Pro Gly Gln Ala
        35                  40                  45

Pro Arg Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Trp Thr Phe Gly Gly Gly Thr Lys Val Glu Ile Lys
            100                 105                 110

<210> SEQ ID NO 52
<211> LENGTH: 121
<212> TYPE: PRT
<213> ORGANISM: Artificial sequence
<220> FEATURE:
<223> OTHER INFORMATION: Humanized mouse Ig

<400> SEQUENCE: 52

Glu Val Gln Leu Val Glu Ser Gly Gly Gly Leu Val Gln Pro Gly Gly
1               5                   10                  15

Ser Leu Lys Leu Ser Cys Ala Ala Ser Gly Phe Thr Phe Ser Asn His
            20                  25                  30

Trp Met His Trp Val Arg Gln Ala Ser Gly Lys Gly Leu Glu Trp Val
        35                  40                  45
```

```
Gly Ala Ile Asp Pro Gly Asn Ser Asp Thr Ser Tyr Asn Gln Lys Phe
 50                  55                  60

Lys Gly Arg Phe Thr Ile Ser Arg Asp Asp Ser Lys Asn Thr Ala Tyr
 65                  70                  75                  80

Leu Gln Met Asn Ser Leu Lys Thr Glu Asp Thr Ala Val Tyr Tyr Cys
                 85                  90                  95

Thr Arg Arg Asp Phe Phe Gly Gly Glu Tyr Ala Val Asp Tyr Trp Gly
                100                 105                 110

Gln Gly Thr Thr Val Thr Val Ser Ser
            115                 120

<210> SEQ ID NO 53
<211> LENGTH: 112
<212> TYPE: PRT
<213> ORGANISM: artificial sequence
<220> FEATURE:
<223> OTHER INFORMATION: humanized mouse Ig

<400> SEQUENCE: 53

Asp Ile Val Met Thr Gln Ser Pro Leu Ser Leu Pro Val Thr Pro Gly
  1               5                  10                  15

Glu Pro Ala Ser Ile Ser Cys Arg Ser Ser Gln Ser Leu Val His Ser
                 20                  25                  30

Asn Gly Asn Thr Tyr Leu His Trp Tyr Leu Gln Lys Pro Gly Gln Ser
             35                  40                  45

Pro Gln Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Ser Gln Ser
                 85                  90                  95

Thr His Val Pro Trp Thr Phe Gly Gln Gly Thr Lys Val Glu Ile Lys
                100                 105                 110

<210> SEQ ID NO 54
<211> LENGTH: 473
<212> TYPE: PRT
<213> ORGANISM: Artificial sequence
<220> FEATURE:
<223> OTHER INFORMATION: Humanized mouse Ig

<400> SEQUENCE: 54

Ala Ala Thr Met Gly Trp Ser Trp Ile Leu Leu Phe Leu Leu Ser Val
  1               5                  10                  15

Thr Ala Gly Val His Ser Gln Val Gln Leu Val Gln Ser Gly Ala Glu
                 20                  25                  30

Val Lys Lys Pro Gly Ala Ser Val Lys Val Ser Cys Lys Ala Ser Gly
             35                  40                  45

Tyr Thr Phe Thr Asn His Trp Met His Trp Val Arg Gln Ala Pro Gly
 50                  55                  60

Gln Gly Leu Glu Trp Met Gly Ala Ile Asp Pro Gly Asn Ser Asp Thr
 65                  70                  75                  80

Ser Tyr Asn Gln Lys Phe Lys Gly Arg Val Thr Met Thr Arg Asp Thr
                 85                  90                  95

Ser Thr Ser Thr Val Tyr Met Glu Leu Ser Ser Leu Arg Ser Glu Asp
                100                 105                 110
```

```
Thr Ala Val Tyr Tyr Cys Ala Arg Arg Asp Phe Phe Gly Gly Glu Tyr
            115                 120                 125
Ala Val Asp Tyr Trp Gly Gln Gly Thr Leu Val Thr Val Ser Ser Ala
        130                 135                 140
Ser Thr Lys Gly Pro Ser Val Phe Pro Leu Ala Pro Ser Ser Lys Ser
145                 150                 155                 160
Thr Ser Gly Gly Thr Ala Ala Leu Gly Cys Leu Val Lys Asp Tyr Phe
                165                 170                 175
Pro Glu Pro Val Thr Val Ser Trp Asn Ser Gly Ala Leu Thr Ser Gly
            180                 185                 190
Val His Thr Phe Pro Ala Val Leu Gln Ser Ser Gly Leu Tyr Ser Leu
        195                 200                 205
Ser Ser Val Val Thr Val Pro Ser Ser Ser Leu Gly Thr Gln Thr Tyr
210                 215                 220
Ile Cys Asn Val Asn His Lys Pro Ser Asn Thr Lys Val Asp Lys Lys
225                 230                 235                 240
Val Glu Pro Lys Ser Cys Asp Lys Thr His Thr Cys Pro Pro Cys Pro
                245                 250                 255
Ala Pro Glu Leu Leu Gly Gly Pro Ser Val Phe Leu Phe Pro Pro Lys
            260                 265                 270
Pro Lys Asp Thr Leu Met Ile Ser Arg Thr Pro Glu Val Thr Cys Val
        275                 280                 285
Val Val Asp Val Ser His Glu Asp Pro Glu Val Lys Phe Asn Trp Tyr
290                 295                 300
Val Asp Gly Val Glu Val His Asn Ala Lys Thr Lys Pro Arg Glu Glu
305                 310                 315                 320
Gln Tyr Asn Ser Thr Tyr Arg Val Val Ser Val Leu Thr Val Leu His
                325                 330                 335
Gln Asp Trp Leu Asn Gly Lys Glu Tyr Lys Cys Lys Val Ser Asn Lys
            340                 345                 350
Ala Leu Pro Ala Pro Ile Glu Lys Thr Ile Ser Lys Ala Lys Gly Gln
        355                 360                 365
Pro Arg Glu Pro Gln Val Tyr Thr Leu Pro Pro Ser Arg Asp Glu Leu
370                 375                 380
Thr Lys Asn Gln Val Ser Leu Thr Cys Leu Val Lys Gly Phe Tyr Pro
385                 390                 395                 400
Ser Asp Ile Ala Val Glu Trp Glu Ser Asn Gly Gln Pro Glu Asn Asn
                405                 410                 415
Tyr Lys Thr Thr Pro Pro Val Leu Asp Ser Asp Gly Ser Phe Phe Leu
            420                 425                 430
Tyr Ser Lys Leu Thr Val Asp Lys Ser Arg Trp Gln Gln Gly Asn Val
        435                 440                 445
Phe Ser Cys Ser Val Met His Glu Ala Leu His Asn His Tyr Thr Gln
450                 455                 460
Lys Ser Leu Ser Leu Ser Pro Gly Lys
465                 470

<210> SEQ ID NO 55
<211> LENGTH: 241
<212> TYPE: PRT
<213> ORGANISM: Artificial sequemce
<220> FEATURE:
<223> OTHER INFORMATION: Humanized mouse Ig
```

<400> SEQUENCE: 55

| | | | | | | | | | | | | | | |
|---|---|---|---|---|---|---|---|---|---|---|---|---|---|---|
|Ala|Ala|Thr|Met|Gly|Trp|Ser|Trp|Ile|Leu|Leu|Phe|Leu|Leu|Ser|Val|
|1| | | |5| | | | |10| | | | |15|

Thr Ala Gly Val His Ser Asp Ile Val Met Thr Gln Ser Pro Leu Ser
                20                  25                  30

Leu Pro Val Thr Pro Gly Glu Pro Ala Ser Ile Ser Cys Arg Ser Ser
            35                  40                  45

Gln Ser Leu Val His Ser Asn Gly Asn Thr Tyr Leu His Trp Tyr Leu
        50                  55                  60

Gln Lys Pro Gly Gln Ser Pro Gln Leu Leu Ile Tyr Lys Val Ser Asn
65                  70                  75                  80

Arg Phe Ser Gly Val Pro Asp Arg Phe Ser Gly Ser Gly Ser Gly Thr
                85                  90                  95

Asp Phe Thr Leu Lys Ile Ser Arg Val Glu Ala Glu Asp Val Gly Val
            100                 105                 110

Tyr Tyr Cys Ser Gln Ser Thr His Val Pro Trp Thr Phe Gly Gln Gly
        115                 120                 125

Thr Lys Val Glu Ile Lys Arg Thr Val Ala Ala Pro Ser Val Phe Ile
    130                 135                 140

Phe Pro Pro Ser Asp Glu Gln Leu Lys Ser Gly Thr Ala Ser Val Val
145                 150                 155                 160

Cys Leu Leu Asn Asn Phe Tyr Pro Arg Glu Ala Lys Val Gln Trp Lys
                165                 170                 175

Val Asp Asn Ala Leu Gln Ser Gly Asn Ser Gln Glu Ser Val Thr Glu
            180                 185                 190

Gln Asp Ser Lys Asp Ser Thr Tyr Ser Leu Ser Ser Thr Leu Thr Leu
        195                 200                 205

Ser Lys Ala Asp Tyr Glu Lys His Lys Val Tyr Ala Cys Glu Val Thr
    210                 215                 220

His Gln Gly Leu Ser Ser Pro Val Thr Lys Ser Phe Asn Arg Gly Glu
225                 230                 235                 240

Cys

<210> SEQ ID NO 56
<211> LENGTH: 1422
<212> TYPE: DNA
<213> ORGANISM: Artificial sequence
<220> FEATURE:
<223> OTHER INFORMATION: Humanized mouse Ig

<400> SEQUENCE: 56

```
gccgccacca tgggctggag ctggatcctg ctgttcctcc tgagcgtgac agcaggagtg      60
cacagccagg tgcagctggt gcagtctggg gctgaggtga agaagcctgg ggcctcagtg     120
aaggtttcct gcaaggcatc tggatacacc ttcaccaacc actggatgca ctgggtgcga     180
caggcccctg acaagggct tgagtggatg ggagctattg atcctggaaa tagtgatact     240
agctacaacc agaagttcaa gggcagagtc accatgacca gggacacgtc cacgagcaca     300
gtctacatgg agctgagcag cctgagatct gaggacacgg ccgtgtatta ctgtgcgagg     360
agggatttct tcggtggtga gtatgctgtg gactactggg gccagggaac cctggtcacc     420
gtctcctcag ctagcaccaa gggcccatcg gtcttccccc tggcaccctc ctccaagagc     480
acctctgggg gcacagcggc cctgggctgc ctggtcaagg actacttccc cgaaccggtg     540
acggtgtcgt ggaactcagg cgccctgacc agcggcgtgc acaccttccc ggctgtccta     600
```

-continued

```
cagtcctcag gactctactc cctcagcagc gtggtgaccg tgccctccag cagcttgggc      660
acccagacct acatctgcaa cgtgaatcac aagcccagca acaccaaggt ggacaagaaa      720
gttgagccca atcttgtga caaaactcac acatgcccac cgtgcccagc acctgaactc      780
ctgggggac cgtcagtctt cctcttcccc ccaaaaccca aggacaccct catgatctcc       840
cggacccctg aggtcacatg cgtggtggtg gacgtgagcc acgaagaccc tgaggtcaag      900
ttcaactggt acgtggacgg cgtggaggtg cataatgcca agacaaagcc gcgggaggag      960
cagtacaaca gcacgtaccg tgtggtcagc gtcctcaccg tcctgcacca ggactggctg     1020
aatggcaagg agtacaagtg caaggtctcc aacaaagccc tcccagcccc catcgagaaa     1080
accatctcca aagccaaagg gcagccccga gaaccacagg tgtacaccct gcccccatcc     1140
cgggatgagc tgaccaagaa ccaggtcagc ctgacctgcc tggtcaaagg cttctatccc     1200
agcgacatcg ccgtggagtg ggagagcaat gggcagccgg agaacaacta caagaccacg     1260
cctcccgtgc tggactccga cggctccttc ttcctctaca gcaagctcac cgtggacaag     1320
agcaggtggc agcaggggaa cgtcttctca tgctccgtga tgcatgaggc tctgcacaac     1380
cactacacgc agaagagcct ctccctgtct ccgggtaaat ga                        1422
```

<210> SEQ ID NO 57
<211> LENGTH: 726
<212> TYPE: DNA
<213> ORGANISM: Artificial sequence
<220> FEATURE:
<223> OTHER INFORMATION: Humanized mouse Ig

<400> SEQUENCE: 57

```
gccgccacca tgggctggag ctggatcctg ctgttcctcc tgagcgtgac agcaggagtg       60
cacagcgata ttgtgatgac tcagtctcca ctctccctgc ccgtcacccc tggagagccg      120
gcctccatct cctgcagatc tagtcagagc cttgtgcaca gtaatggaaa cacctattta      180
cattggtacc tgcagaagcc agggcagtct ccacagctcc tgatctataa agtttccaac      240
cgatttctg gggtccctga caggttcagt ggcagtggat caggcacaga ttttacactg      300
aaaatcagca gagtggaggc tgaggatgtt ggggtttatt actgctctca aagtacacat      360
gttccgtgga cgttcggcca agggaccaag gtggaaatca aacgaacggt ggctgcacca      420
tctgtcttca tcttcccgcc atctgatgag cagttgaaat ctggaactgc ctctgttgtg      480
tgcctgctga ataacttcta tcccagagag gccaaagtac agtggaaggt ggataacgcc      540
ctccaatcgg gtaactccca ggagagtgtc acagagcagg acagcaagga cagcacctac      600
agcctcagca gcaccctgac gctgagcaaa gcagactacg agaaacacaa agtctacgcc      660
tgcgaagtca cccatcaggg cctgagctcg cccgtcacaa agagcttcaa caggggagag      720
tgttag                                                                726
```